(12) United States Patent
Harth et al.

(10) Patent No.: US 10,308,774 B2
(45) Date of Patent: Jun. 4, 2019

(54) POLYCARBONATE CONTAINING COMPOUNDS AND METHODS RELATED THERETO

(71) Applicant: Vanderbilt University, Nashville, TN (US)

(72) Inventors: Eva M. Harth, Nashville, TN (US); David M. Stevens, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 15/443,456

(22) Filed: Feb. 27, 2017

(65) Prior Publication Data

US 2017/0166710 A1 Jun. 15, 2017

Related U.S. Application Data

(63) Continuation of application No. 14/399,920, filed as application No. PCT/US2013/040192 on May 8, 2013, now Pat. No. 9,580,548.

(60) Provisional application No. 61/644,241, filed on May 8, 2012.

(51) Int. Cl.
| | |
|---|---|
| *C08G 64/02* | (2006.01) |
| *C08G 64/42* | (2006.01) |
| *C08G 59/32* | (2006.01) |
| *C08J 3/24* | (2006.01) |
| *C08K 5/37* | (2006.01) |
| *C08G 59/66* | (2006.01) |
| *C08G 59/34* | (2006.01) |
| *C08G 59/50* | (2006.01) |
| *A61L 31/06* | (2006.01) |
| *A61L 31/14* | (2006.01) |
| *A61L 31/16* | (2006.01) |
| *A61K 9/06* | (2006.01) |
| *A61K 47/34* | (2017.01) |
| *A61K 9/51* | (2006.01) |
| *C08J 3/075* | (2006.01) |
| *A61K 9/19* | (2006.01) |

(52) U.S. Cl.
CPC .......... *C08J 3/246* (2013.01); *A61K 9/06* (2013.01); *A61K 9/5146* (2013.01); *A61K 9/5192* (2013.01); *A61K 47/34* (2013.01); *A61L 31/06* (2013.01); *A61L 31/146* (2013.01); *A61L 31/16* (2013.01); *C08G 59/34* (2013.01); *C08G 59/504* (2013.01); *C08G 59/66* (2013.01); *C08G 64/0216* (2013.01); *C08G 64/0241* (2013.01); *C08G 64/0291* (2013.01); *C08G 64/42* (2013.01); *C08J 3/075* (2013.01); *C08K 5/37* (2013.01); *A61K 9/19* (2013.01); *A61L 2300/412* (2013.01); *A61L 2300/416* (2013.01); *A61L 2400/12* (2013.01); *C08J 2369/00* (2013.01)

(58) Field of Classification Search
None
See application file for complete search history.

(56) References Cited

U.S. PATENT DOCUMENTS

| | | | |
|---|---|---|---|
| 3,280,078 A | 10/1966 | Fritz et al. | |
| 3,728,400 A * | 4/1973 | Michelotti | ............ C07C 321/00 |
| | | | 528/109 |
| 5,889,125 A | 3/1999 | Neumann et al. | |
| 5,945,464 A | 8/1999 | Takushima et al. | |
| 6,043,334 A | 3/2000 | Kanamaru et al. | |
| 6,391,983 B1 | 5/2002 | Bateman et al. | |
| 9,580,548 B2 | 2/2017 | Harth et al. | |
| 2003/0144373 A1 | 7/2003 | Bowman et al. | |
| 2006/0047031 A1 | 3/2006 | Cella et al. | |
| 2008/0102114 A1 | 5/2008 | Koritala et al. | |
| 2011/0274620 A1 | 11/2011 | Harth et al. | |

FOREIGN PATENT DOCUMENTS

| | | |
|---|---|---|
| WO | PCT/US2013/040192 | 5/2013 |
| WO | WO 2013/169938 | 11/2013 |
| WO | WO-2013/169938 A2 | 11/2013 |

OTHER PUBLICATIONS

Albertsson, A.C., Aliphatic Polyesters: Synthesis, Properties and Applications. Adv Polym Sci. 157:1-40 (2002).
Beck, J. B. et al., Facile Preparation of Nanoparticles by Intramolecular Crosslinking of Isocyanate Functionalized Copolymers, Macromolecules. 42(15): 5629-35 (2009).
Bourissou, D., et al., Recent advances in the controlled preparation of poly($\alpha$-hydroxy acids): Metal-free catalysts and new monomers. C.R. Chimie. 10(9):775-94 (2007).
Dove, A. P. et al., N-Heterocyclic carbenes: Effective organic catalysts for living polymerization. Polymer. 47(11):4018-25 (2006).
Drumright, R. E. et al., Polylactic Aci Technology. Adv Matter. 12(23):1841-6 (2000).
Hu, X., et al., Synthesis and Characterization of Amphiphilic Block Copolymers with Allyl Side-Groups. J Polym Sci, Part A: Polym Chem. 45(23):5518-28 (2007).
Kamber, N. E. et al., Organocatalytic Ring-Opening Polymerization. Chem Rev. 107: 5813-40 (2007).
Martina, M.et al., Biodegradable polymers applied in tissue engineering research: a review. Polym Int. 56:145-57 (2007).
Montarnal et al., Silica-Like Malleable Materials from Permanent Organic Networks. Science. 334:965-8 (2011).
Mullen, B. D. et al., New Aliphatic Poly(ester-carbonates) Based on 5-Methyl-5-allyloxycarbonyl-1,3-dioxan-2-one. J Polym Sci Pol Chem. 41:1978-91 (2003).
Passarella, R.J. et al., Targeted nanoparticles that deliver a sustained, specific release of paclitaxel to irradiated tumors. Cancer Res. 70:4550-9 (2010).

(Continued)

*Primary Examiner* — David J Buttner
(74) *Attorney, Agent, or Firm* — Ballard Spahr LLP

(57) ABSTRACT

Disclosed herein are crosslinked polycarbonates, composition thereof and methods thereof. The crosslinked polycarbonates can be prepared from allyl or epoxy polycarbonates. This abstract is intended as a scanning tool for purposes of searching in the particular art and is not intended to be limiting of the present invention.

20 Claims, 15 Drawing Sheets

(56) References Cited

OTHER PUBLICATIONS

Pratt, R. et al., Exploration, Optimization, and Application of Supramolecular Thiourea-Amine Catalysts for the Synthesis of Lactide (Co)polymers. Macromolecules. 39:7863-71 (2006).
Rokicki, G.,Aliphatic cyclic carbonates and spiroorthocarbonates as monomers. Prog Polym Sci. 25:259-342 (2000).
Ryu, J. H. et al., Self-Cross-Linked Polymer Nanogels: A Versatile Nanoscopic Drug Delivery Platform. J Am Chem Soc. 132:17227-35 (2010).
Ryu, J. H., et al., Surface-Functionalizable Polymer Nanogels with Facile Hydrophobic Guest Encapsulation Capabilities. J Am Chem Soc. 132: 8246-7 (2010).
Sanders, D.P. et al., A Simple and Efficient Synthesis of Functionalized Cyclic Carbonate Monomers Using a Versatile Pentafluorophenyl Ester Intermediate. J Am Chem Soc. 132:14724-6 (2010).
Seo, M.et al., Polymeric Nanoparticles via Noncovalent Cross-Linking of Linear Chains. Macromolecules. 41: 6413-8 (2008).
Templaar et al., Organocatalytic Synthesis and Postpolymerization Functionalization of Allyl-Functional Poly(carbonate)s. Macromolecules. 44(7): 2084-91 (2011).
Uhrich, K. E. et al., Polymeric Systems for Controlled Drug Release. Chem Rev. 99:3181-98 (1999).
Van der Ende, A.E. et al., "Click" Reactions: Novel Chemistries for Forming Well-defined Polyester Nanoparticles. Macromolecules. 43:5665-71 (2010).
Van der Ende, A.E. et al., Approach to Formation of Multifunctional Polyester Particles in Controlled Nanoscopic Dimensions. J Am Chem Soc. 130: 8706 (2008).
Van der Ende, A.E. et al., Linear release nanoparticle devices for advanced targeted cancer therapies with increased efficacy. Polymer Chemistry. 1:93-6 (2010).
Van der Ende, A. et al., Tailored polyester nanoparticles: post-modification with dendritic transporter and targeting units via reductive amination and thiol-ene chemistry. Soft Matter. 5: 1417-25 (2009).
Wang, R. et al., Unprecedented Access to Functional Biodegradable Polymers and Coatings. Macromolecules. 44:6009-16 (2011).
Xu, J. et al., A Versatile Monomer for Preparing Well-Defined Functional Polycarbonates and Poly(ester-carbonates). Macromolecules. 44: 2660-7 (2011).

International Search Report and Written Opinion dated Oct. 31, 2013 by the International Searching Authority for International Patent Application No. PCT/US2013/040192, which was published as WO 2013/169938 on Nov. 14, 2013 (Inventors—Harth et al.; Applicant—Vanderbilt Univ.) (13 pages).
International Preliminary Report on Patentability dated Nov. 11, 2014 by the International Searching Authority for International Patent Application No. PCT/US2013/040192, which was published as WO 2013/169938 on Nov. 14, 2013 (Inventors—Harth et al.; Applicant—Vanderbilt Univ.) (7 pages).
Requirement for Restriction/Election dated Dec. 14, 2015 by the USPTO for U.S. Appl. No. 14/399,920, filed Nov. 7, 2014 and granted as U.S. Pat. No. 9,580,548 on Feb. 28, 2017 (Inventors—Harth et al.; Applicant—Vanderbilt Univ.) (9 pages).
Response to Requirement for Restriction/Election dated Feb. 15, 2016 to the USPTO for U.S. Appl. No. 14/399,920, filed Nov. 7, 2014 and granted as U.S. Pat. No. 9,580,548 on Feb. 28, 2017 (Inventors—Harth et al.; Applicant—Vanderbilt Univ.) (9 pages).
Non Final Rejection dated Mar. 2, 2016 by the USPTO for U.S. Appl. No. 14/399,920, filed Nov. 7, 2014 and granted as U.S. Pat. No. 9,580,548 on Feb. 28, 2017 (Inventors—Harth et al.; Applicant—Vanderbilt Univ.) (9 pages).
Response to Non Final Rejection dated Sep. 2, 2016 to the USPTO for U.S. Appl. No. 14/399,920, filed Nov. 7, 2014 and granted as U.S. Pat. No. 9,580,548 on Feb. 28, 2017 (Inventors—Harth et al.; Applicant—Vanderbilt Univ.) (119 pages).
Notice of Allowance dated Oct. 18, 2016 by the USPTO for U.S. Appl. No. 14/399,920, filed Nov. 7, 2014 and granted as U.S. Pat. No. 9,580,548 on Feb. 28, 2017 (Inventors—Harth et al.; Applicant—Vanderbilt Univ.) (7 pages).
Issue Notification dated Feb. 8, 2017 by the USPTO for U.S. Appl. No. 14/399,920, filed Nov. 7, 2014 and granted as U.S. Pat. No. 9,580,548 on Feb. 28, 2017 (Inventors—Harth et al.; Applicant—Vanderbilt Univ.) (1 page).
Certificate of Correction dated Jul. 18, 2017 by the USPTO for U.S. Appl. No. 14/399,920, filed Nov. 7, 2014 and granted as U.S. Pat. No. 9,580,548 on Feb. 28, 2017 (Inventors—Harth et al.; Applicant—Vanderbilt Univ.) (2 pages).
U.S. Appl. No. 61/644,241, filed May 8, 2012, Eva M. Harth.
U.S. Appl. No. 14/399,920, filed May 8, 2013, Eva M. Harth.

* cited by examiner

POLYCARBONATE CONTAINING COMPOUNDS AND METHODS RELATED THERETO

CROSS-REFERENCE TO RELATED APPLICATIONS

This Application is a continuation of U.S. application Ser. No. 14/399,920, filed Nov. 7, 2014, now U.S. Pat. No. 9,580,548, which is a National Stage of International Application No. PCT/US2013/040192, filed May 8, 2013, which claims the benefit of U.S. Provisional Application No. 61/644,241, filed on May 8, 2012, which is incorporated herein by reference in its entirety.

STATEMENT REGARDING FEDERALLY SPONSORED RESEARCH

This invention was made with U.S. government support under grant number CHE-0645737, awarded by the National Science Foundation (NSF), and under grant number 5T32GM007628-33, awarded by the Pharmacology Training Grant under a National Institute of Health (NIH) Training Grant. The U.S. government has certain rights in the invention.

BACKGROUND

A range of degradable polymers have been investigated for in vivo applications.[10-13] Poly(ester)s are most commonly studied, however the introduction of side-chain functional groups is typically challenging and can limit their applicability in advanced applications.[13,14] Poly(carbonate)s prepared by the ring-opening polymerization (ROP) of 6-membered cyclic monomers have been widely explored for these applications and organocatalysis has provided efficient routes to realize a range of functionalized polymer structures.[15-17] Recently, the exploration of a range of functional monomers and polymers has been explored from simple precursors giving access to unprecedented levels of functional group incorporation.[18-20] Importantly, poly(carbonate) materials display slower degradation profiles with less toxic byproducts than poly(ester)s thus making them ideal candidates as one of the building blocks for advanced nanomaterials.[14]

Accordingly, described herein are poly(carbonate)s suitable for nanomaterials.

SUMMARY OF THE INVENTION

In accordance with the purpose(s) of the invention, as embodied and broadly described herein, the invention, in one aspect, relates to crosslinked polycarbonates, composition thereof and methods thereof.

Disclosed herein are compounds comprising a first and second allyl functionalized polycarbonate. Also disclosed herein are compounds comprising a crosslinked first and second allyl functionalized polycarbonate.

Also disclosed herein are compounds comprising a first and second epoxy functionalized polycarbonate. Also disclosed herein are compounds comprising a crosslinked first and second epoxy functionalized polycarbonate.

Also disclosed herein are methods of crosslinking polycarbonates comprising a) Providing a first and second allyl functionalized polycarbonate; and b) Crosslinking the first and second allyl functionalized polycarbonate via a crosslinker.

Also disclosed herein are methods of crosslinking polycarbonates comprising a) Providing a first and second epoxy functionalized polycarbonate; and b) Crosslinking the first and second epoxy functionalized polycarbonate via a crosslinker.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
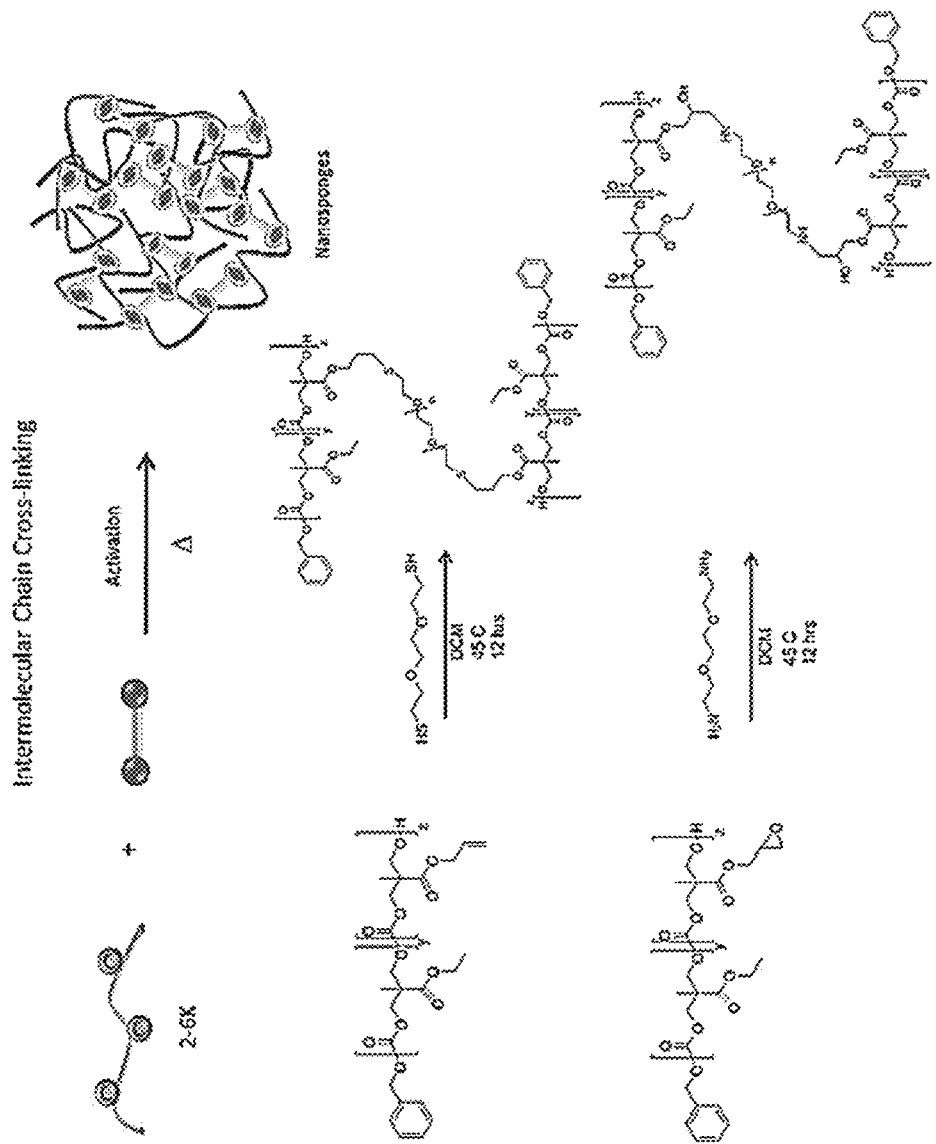
FIG. 1 shows nanoparticle formation via an intermolecular thiolene-click reaction and the epoxide-a mine reaction with either P[(MAC)$_z$-co-(MTC-Et)$_y$] or the oxidized version.
Figure 2A:
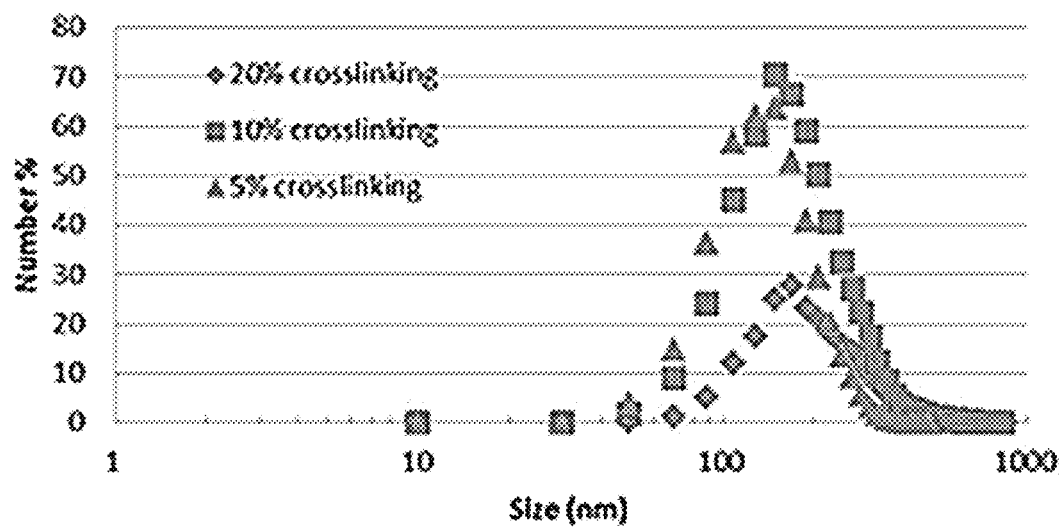
FIGS. 2A and 2B show the DLS analysis data for both particles prepared with amine-epoxide and the thiolene-click reaction along with the corresponding TEM imagines of both particle systems: 2A: 5% amine-epoxide and 2B: 5% thiolene-click.
Figure 2A:
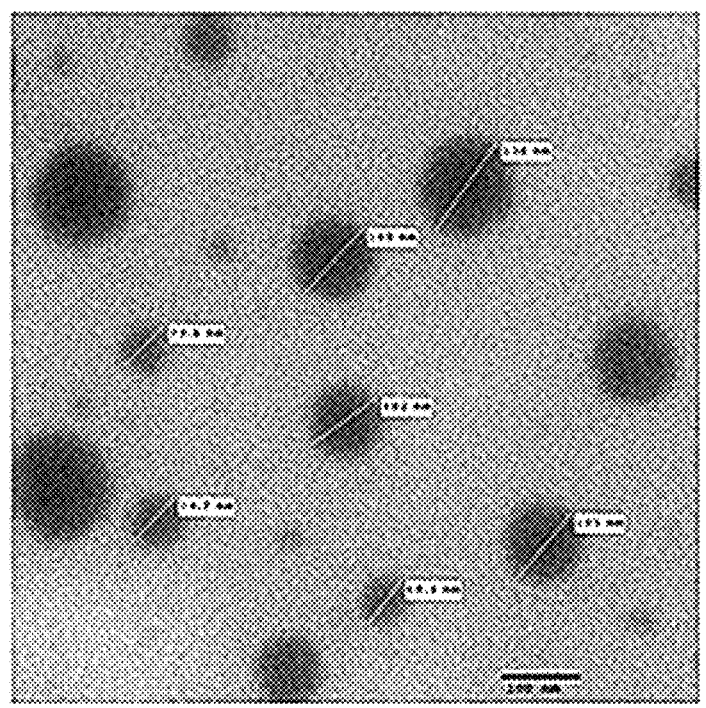
Figure 2B:
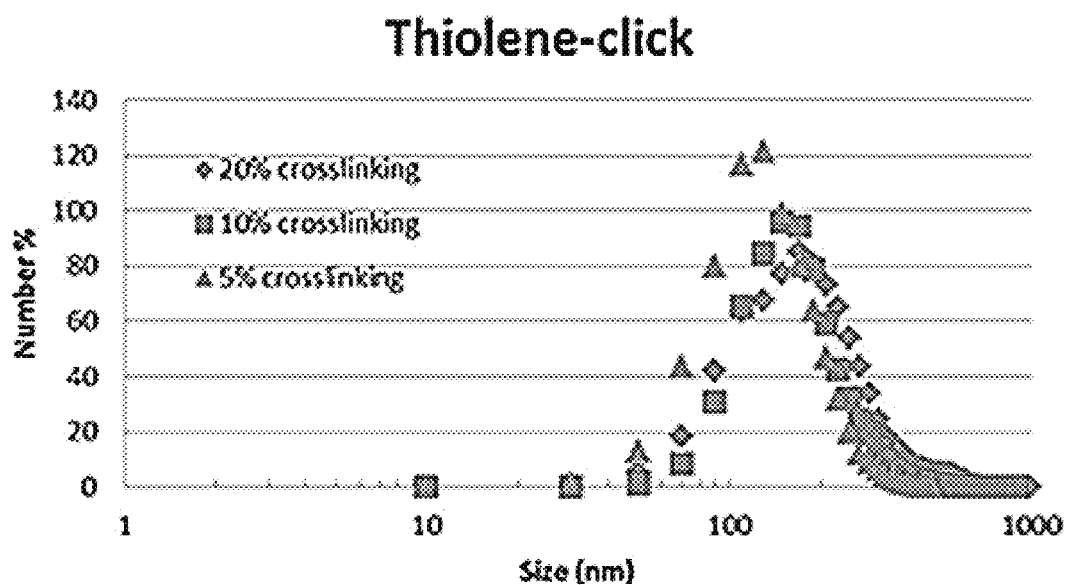
Figure 2B:
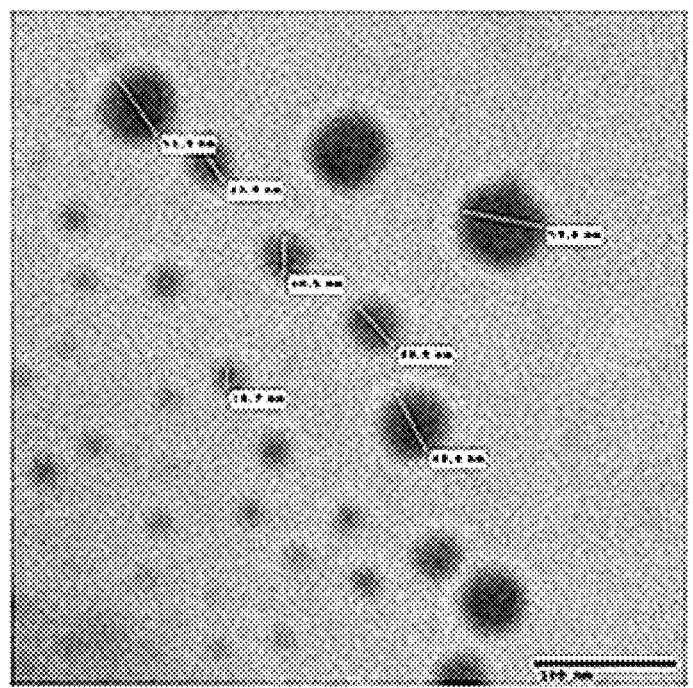

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" refers to the target of administration, e.g. an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, fish, bird, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more muscle disorders prior to the administering step. In some aspects of the disclosed method, the subject has been diagnosed with a need for promoting muscle health prior to the administering step. In some aspects of the disclosed method, the subject has been diagnosed with a need for promoting muscle health prior, promote normal muscle function, and/or promote healthy aging muscles to the administering step.

As used herein, the term "treatment" refers to the medical management of a patient with the intent to cure, ameliorate, stabilize, or prevent a disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, fish, bird, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can treat or prevent cancer. As a further example, "diagnosed with a need for treating or preventing cancer" refers to having been subjected to a physical examination by a person of skill, for example, a physician, and found to have a condition characterized by cancer or other disease wherein treating or preventing cancer would be beneficial to the subject. Such a diagnosis can be in reference to a disorder, such as cancer or duodenal ulcers, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to cancer) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in a in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein a gene or genes has been introduced or knocked-out, as appropriate, to replicate a disease process.

As used herein, "$IC_{50}$," is intended to refer to the concentration or dose of a substance (e.g., a compound or a drug) that is required for 50% inhibition or diminuation of a biological process, or component of a process, including a protein, subunit, organelle, ribonucleoprotein, etc. $IC_{50}$ also refers to the concentration or dose of a substance that is required for 50% inhibition or diminuation in vivo, as further defined elsewhere herein. Alternatively, $IC_{50}$ also refers to the half maximal (50%) inhibitory concentration (IC) or inhibitory dose of a substance. The response can be measured in a in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the terms "linker" and "crosslinker" are used interchangeably.

B. Compounds and Compositions

For the first time described herein is the formation of functionalized poly(carbonate) particles with an established intermolecular cross-linking process. Six types of 'nanosponges' were prepared with the differentiation in crosslinking density and crosslinking chemistry. The intermolecular chain crosslinking process was investigated via the epoxide amine reaction and the thiol-ene click reaction. Well-defined functionalized polycarbonate copolymers from organocatalytic synthesis and Sn(OTf)$_2$ metal catalyzed reactions were critical to perform controlled crosslinking reactions to give particles in nanoscopic sizes of 150-220 nm for the thiolene-click reaction and 160-230 nm for the epoxide amine reaction. The resulting nanoscopic sizes are a result of the chosen equivalencies of the diamine or dithiol-crosslinking partner to provide an example of the intermolecular cross-linking reaction.

Disclosed herein are compounds comprising a first and second allyl functionalized polycarbonate. Also disclosed herein are compounds comprising a crosslinked first and second allyl functionalized polycarbonate. Also disclosed herein are compounds comprising a first allyl functionalized polycarbonate.

Disclosed herein are compounds comprising a first and second epoxy functionalized polycarbonate. Also disclosed herein are compounds comprising a crosslinked first and second epoxy functionalized polycarbonate. Also disclosed herein are compounds comprising a first epoxy functionalized polycarbonate.

Also disclosed herein are nanosponges comprising the disclosed compounds. Also disclosed herein are nanoparticles comprising the disclosed compounds. Also disclosed herein are macroscopic networks comprising the disclosed compounds. Also disclosed herein are hydrogels comprising the disclosed compounds.

In one aspect, the compounds comprise a crosslinker.

In one aspect, the crosslinker comprises at least two moieties that can be reacted with an allyl. In another aspect, the crosslinker comprises at least two moieties that can be reacted with an epoxy. In yet another aspect, the crosslinker comprises at least one moiety that can be reacted with an epoxy and at least one moiety that can be reacted with an allyl. In yet another aspect, the crosslinker comprises at least one amine moiety. In yet another aspect, the crosslinker comprises at least two amine moieties. In yet another aspect, the crosslinker comprises at least one thiol moiety. In yet another aspect, the crosslinker comprises at least two thiol moieties. In yet another aspect, the crosslinker comprises at least one thiol moiety and at least one amine moiety.

In one aspect, the crosslinker comprises one or more ether bonds. In another aspect, the crosslinker comprises two ether bonds.

In yet another aspect, the crosslinker has the structure

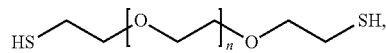

wherein n is from 1 to 1000.

In yet another aspect, the crosslinker has the structure

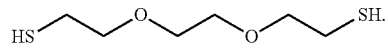

In yet another aspect, the crosslinker has the structure

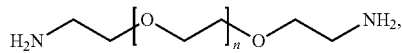

wherein n is from 1 to 1000.

In yet another aspect, the crosslinker has the structure

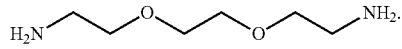

In one aspect, the first and second allyl functionalized polycarbonate are the same. In another aspect, the first and second allyl functionalized polycarbonates are the different.

In one aspect, the first and second allyl functionalized polycarbonate are copolymers.

In one aspect, the first and second epoxy functionalized polycarbonate are the same. In another aspect, the first and second epoxy functionalized polycarbonates are the different.

In one aspect, the first and second epoxy functionalized polycarbonate are copolymers.

In one aspect the first and/or second allyl functionalized polycarbonate can be a co-polymer. The copolymer comprises at least one part allyl monomer and at least one part non-allyl monomer. The non-allyl monomer does not react with the crosslinker. In one aspect, the non-allyl monomer is present in a larger amount than the allyl monomer in the copolymer. For example, the non-allyl monomer can be present at least in 60%, 70%, 75%, 80%, 85%, 90%, 95% or 98% in the copolymer.

In one aspect the first and/or second epoxy functionalized polycarbonate can be a co-polymer. The copolymer comprises at least one part epoxy monomer and at least one part non-epoxy monomer. The non-epoxy monomer does not react with the crosslinker. In one aspect, the non-epoxy monomer is present in a larger amount than the epoxy monomer in the copolymer. For example, the non-epoxy monomer can be present at least in 60%, 70%, 75%, 80%, 85%, 90%, 95% or 98% in the copolymer.

In one aspect, the wherein the first allyl functionalized polycarbonate has the formula

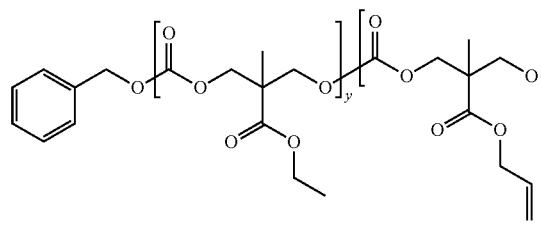

wherein y is 1 to 1000 and z is 1 to 1000.

In one aspect, the wherein the second allyl functionalized polycarbonate has the formula

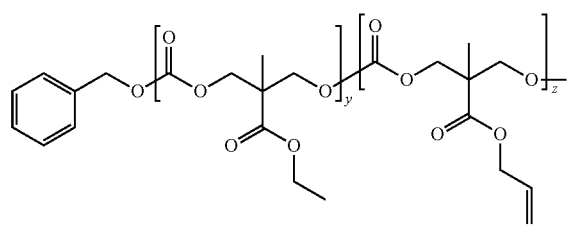

wherein y is 1 to 1000 and z is 1 to 1000.

In one aspect, the crosslinked polycarbonate has the structure

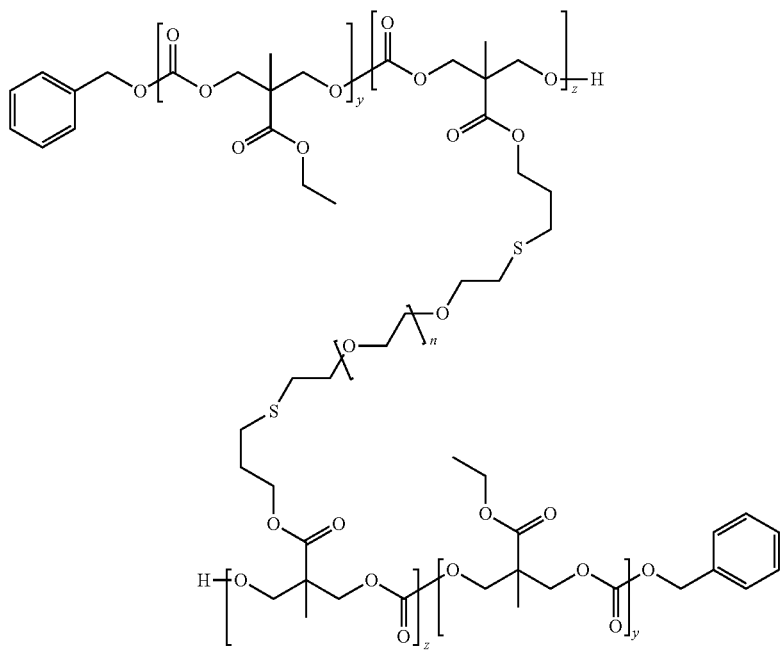

wherein each y is individually 1 to 1000, each z is individually 1 to 1000, and n is 1 to 1000.

In one aspect, the first epoxy functionalized polycarbonate has the structure

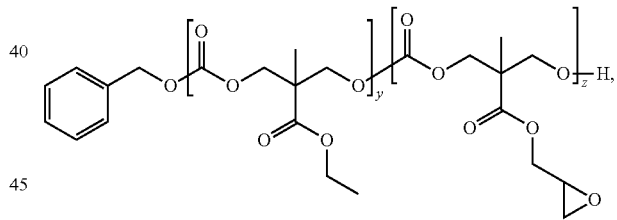

whereie y is 1 to 1000 and z is 1 to 1000.

In one aspect, the second epoxy functionalized polycarbonate has the structure

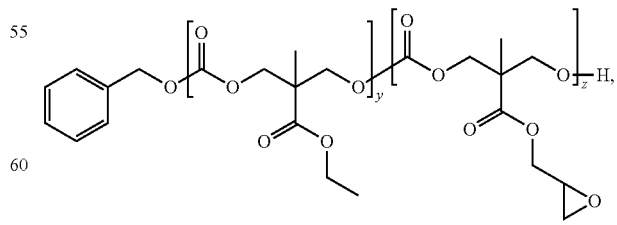

wherein y is 1 to 1000 and z is 1 to 1000.

In one aspect, the crosslinked polycarbonate has the structure

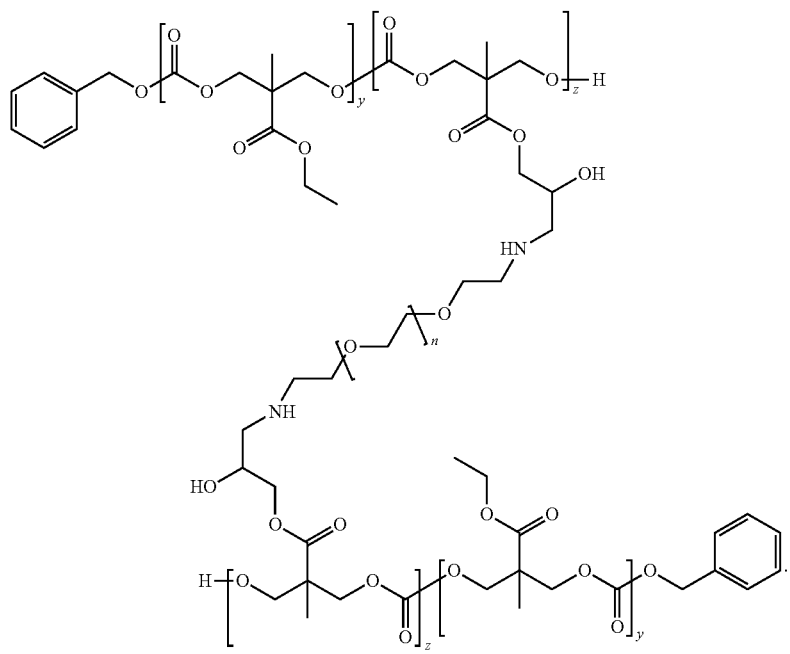

In one aspect, y is 1 to 1000. In another aspect, y is 1 to 500. In yet another aspect, y is 1 to 300. In yet another aspect, y is 1 to 100. In yet another aspect, y is 1 to 50. In yet another aspect, y is 1 to 25.

In one aspect, z is 1 to 1000. In another aspect, z is 1 to 500. In yet another aspect, z is 1 to 300. In yet another aspect, z is 1 to 100. In yet another aspect, z is 1 to 50. In yet another aspect, z is 1 to 25.

In another aspect, y is 1 to 500 and z is 1 to 500. In yet another aspect, y is 1 to 300 and z is 1 to 300. In yet another aspect, y is 1 to 100 and z is 1 to 100. In yet another aspect, y is 1 to 50 and z is 1 to 50. In yet another aspect, y is 1 to 25 and z is 1 to 25.

In one aspect, n is 1 to 500. In yet another aspect, n is 1 to 300. In yet another aspect, n is 1 to 100. In yet another aspect, n is 1 to 50. In yet another aspect, n is 1 to 25.

In one aspect, the first allyl functionalized polycarbonate comprises at least 75% y. In another aspect, the first allyl functionalized polycarbonate comprises at least 80% y. In yet another aspect, the first allyl functionalized polycarbonate comprises at least 85% y. In yet another aspect, the first allyl functionalized polycarbonate comprises at least 90% y. In yet another aspect, the first allyl functionalized polycarbonate comprises at least 95% y.

In one aspect, the first epoxy functionalized polycarbonate comprises at least 75% y. In another aspect, the first epoxy functionalized polycarbonate comprises at least 80% y. In yet another aspect, the first epoxy functionalized polycarbonate comprises at least 85% y. In yet another aspect, the first epoxy functionalized polycarbonate comprises at least 90% y. In yet another aspect, the first epoxy functionalized polycarbonate comprises at least 95% y.

In one aspect, the compounds disclosed herein can comprise a targeting peptide. The targeting peptide can be covalently bonded to the compound. In one aspect, the targeting peptide can be covalently bonded to a crosslinker. In one aspect, the compound comprises a crosslinked first and second epoxy functionalized polycarbonate and a targeting peptide covalently bonded to a crosslinker. In another aspect, the compound comprises a crosslinked first and second allyl functionalized polycarbonate and a targeting peptide covalently bonded to a crosslinker.

In one aspect, the targeting peptide is a cancer targeting peptide. Such cancer targeting peptides are known in the art. In one aspect, the cancer targeting peptide is N-methylmorpholine.

In one aspect, the compound has the structure

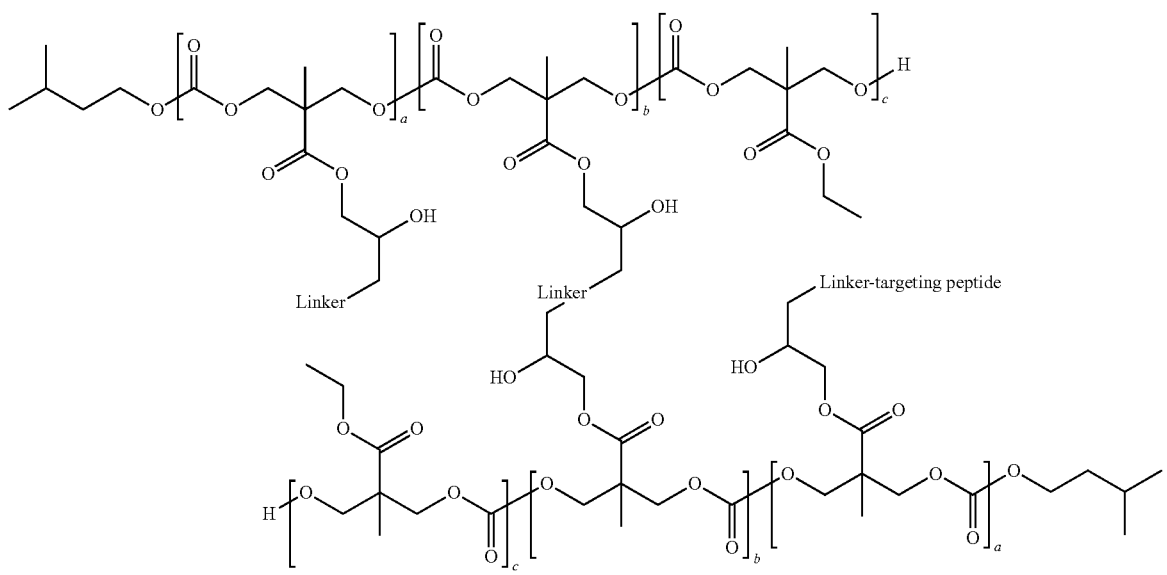

wherein each a is individually 1 to 1000, each b is individually 1 to 1000, and each c is 1 to 1000.

In another aspect, the compound has the structure

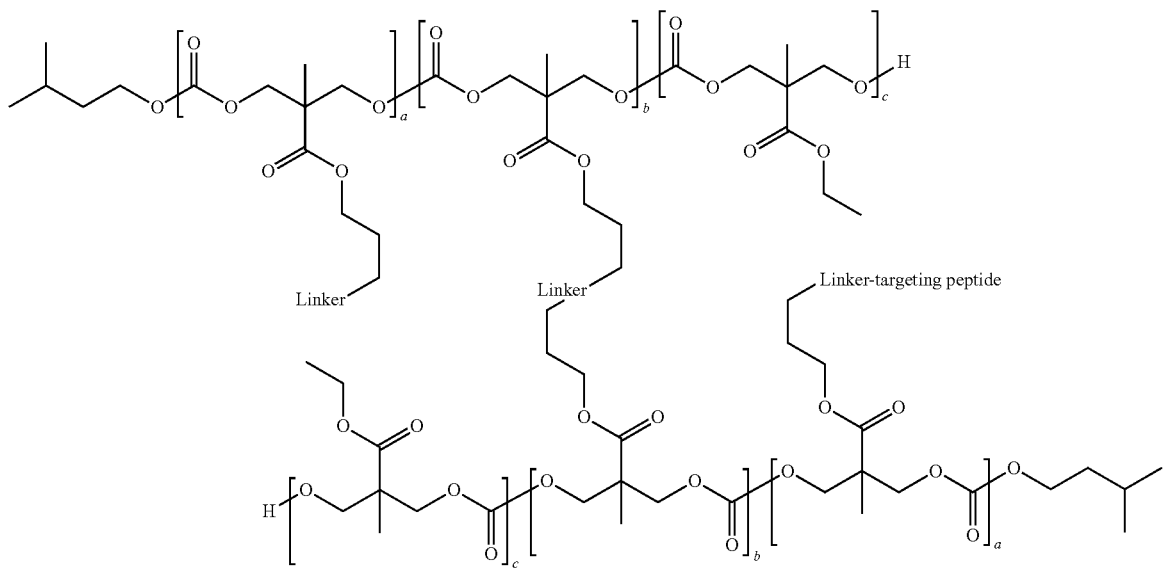

wherein each a is individually 1 to 1000, each b is individually 1 to 1000, and each c is 1 to 1000.

In one aspect, a is 1 to 1000. In another aspect, a is 1 to 500. In yet another aspect, a is 1 to 300. In yet another aspect, a is 1 to 100. In yet another aspect, a is 1 to 50. In yet another aspect, a is 1 to 25.

In one aspect, b is 1 to 1000. In another aspect, b is 1 to 500. In yet another aspect, b is 1 to 300. In yet another aspect, b is 1 to 100. In yet another aspect, b is 1 to 50. In yet another aspect, b is 1 to 25.

In one aspect, c is 1 to 1000. In another aspect, c is 1 to 500. In yet another aspect, c is 1 to 300. In yet another aspect, c is 1 to 100. In yet another aspect, c is 1 to 50. In yet another aspect, c is 1 to 25.

Also disclosed is a nanoparticle comprising the compounds comprising a crosslinked first and second epoxy functionalized polycarbonate and a targeting peptide covalently bonded to a crosslinker. In one aspect, the nanoparticle can further comprise a therapeutic agent, prophylactic agent, or diagnostic agent, or a mixture thereof. In one aspect, the nanoparticle further comprises a cancer therapeutic agent, such as paclitaxel.

In one aspect, the crosslinked polycarbonate disclosed herein is a nanosponge. In another aspect, the crosslinked polycarbonate disclosed herein is a nanoparticle. In yet another aspect, the crosslinked polycarbonate disclosed herein is a macroscopic network.

In one aspect, the compounds and compositions disclosed herein can comprise a hydroxyl terminated polymer, such a hydroxyl terminated PEG. The hydroxyl terminated polymer can be hydrophilic. In one aspect, the hydroxyl terminated polymer can be covalently bonded to the compound.

In one aspect, the compound can have the structure

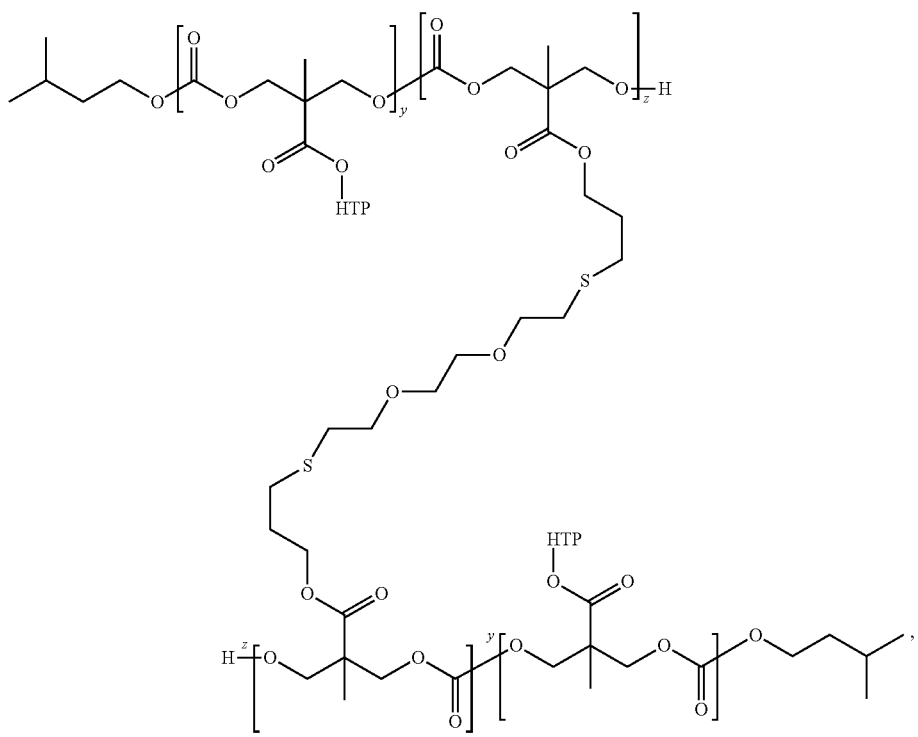

wherein each y independently is 1 to 1000 and each z independently is 1 to 1000.

Also disclosed herein are macroscopic networks comprising the disclosed compounds comprising a hydroxyl terminated polymer. These macroscopic networks can be altered via reversible trans-esterification reactions, thereby changing the properties of the macroscopic network. An example of such technology is described by Montarnal et al. (*Science*, 334, 965 (2011), which is hereby incorporated by references in its entirety.

Also disclosed is a pharmaceutical composition comprising a compound or composition disclosed herein and an effective amount of a therapeutic agent, prophylactic agent, or diagnostic agent, or a mixture thereof, and a pharmaceutically acceptable carrier. In one aspect, the disclosed compounds and pharmaceutical compositions can be co-administered with one or more therapeutic agents, prophylactic agents, or diagnostic agents.

C. Methods of Making Compound and Compositions

Disclosed herein is a method of crosslinking polycarbonates comprising: a) providing a first and second allyl functionalized polycarbonate; and b) crosslinking the first and second allyl functionalized polycarbonate via a crosslinker.

Also disclosed herein is a method of crosslinking polycarbonates comprising: a) providing a first and second epoxy functionalized polycarbonate; and b) crosslinking the first and second epoxy functionalized polycarbonate via a crosslinker.

Also disclosed herein is a method of crosslinking polycarbonates comprising: a) providing a first epoxy functionalized polycarbonate; b) providing a first allyl functionalized polycarbonate; and c) crosslinking the first epoxy functionalized polycarbonate and the first allyl functionalized polycarbonate via a crosslinker.

In one aspect, the methods comprise the use of a Sn catalyst.

Disclosed herein are compounds made from the methods disclosed herein. Also disclosed are composition comprising compounds made from the methods disclosed herein. Also disclosed are nanoparticles comprising compounds made from the methods disclosed herein.

D. Methods of Use

Also disclosed herein is a method of delivering a therapeutic agent, prophylactic agent, or diagnostic agent to a subject in need thereof comprising administering a composition comprising a compound or composition disclosed herein comprising a therapeutic agent, prophylactic agent, or diagnostic agent. In one aspect, the composition is a nanosponge or nanoparticle. In another aspect, the composition is a macroscopic network. In yet another aspect, the composition is a pharmaceutical composition as disclosed herein. In one aspect, the administration is oral administration.

In one aspect, the subject has been diagnosed with a need for the administration of a therapeutic agent, prophylactic agent, or diagnostic agent.

E. Manufacture of a Medicament

In one aspect, the invention relates to a method for the manufacture of a medicament for treating or preventing a disease, such as cancer, comprising combining a therapeutically effective amount of a disclosed compound or compositions or product of a disclosed method with a pharmaceutically acceptable carrier or diluent.

In a further aspect, the medicament comprises a disclosed compound or composition.

F. Kits

Also disclosed herein are kits comprising one or more of the disclosed compounds or compositions, and one or more of: a) at least one cancer agent, b) instructions for treating a disorder associated with cancer, or c) instructions for administering the one or more disclosed compounds or compositions.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases are commercially available, or can be prepared according to literature procedures or as illustrated herein.

The following exemplary compounds of the invention were synthesized. The Examples are provided herein to illustrate the invention, and should not be construed as limiting the invention in any way.

a. Example 1

(a) Experimental Section:

Materials. $CDCl_3$ and (−)-sparteine were dried over $CaH_2$, distilled, degassed and stored under inert atmosphere. Benzyl alcohol was dried and stored over 4 Å molecular sieves under inert atmosphere. Methylene chloride was purified over an Innovative Technology SPS alumina solvent column and degassed before use. 5-Methyl-5-allyloxycarbonyl-1,3-dioxan-2-one (MAC) was synthesized as reported previously by Hu, X et al (*J. Polym. Sci., Part A: Polym. Chem.* 2007, 45, 5518-5528), recrystallized several times before use and dried over $CaH_2$ in dry THF at 50-60° C. 1-(3,5-Bis(trifluoromethyl)phenyl)-3-cyclohexylthiourea was synthesized as previously reported by Pratt, R et al. (*Macromolecules* 2006, 39, 7863-7871) then dried over calcium hydride in dry tetrahydrofuran and recrystallized from dry methylene chloride. Silica Gel (pore size=40 Å) was obtained from Fisher Scientific and used as received. All other solvents and chemicals were obtained from Sigma Aldrich or Fisher Scientific and used as received.

General considerations. Polymerizations were performed under inert atmosphere in a glovebox. $^1H$ NMR and $^{13}C$ NMR spectra at Warwick were recorded on a Bruker DPX-300, DPX-400, DRX-500 or AV II-700 spectrometer at 293K. Chemical shifts are reported as $\delta$ in parts per million (ppm) and referenced to the residual solvent signal ($CDCl_3$: $^1H$, $\delta$=7.26 ppm; $^{13}C$, $\delta$=77.16 ppm; $(CD_3)_2SO$: $^1H$, $\delta$=2.50; $^{13}C$, $\delta$=39.52). Gel-permeation chromatography (GPC) was used to determine the molecular weights and polydispersities of the synthesized polymers. GPC in THF was conducted on a system composed of a Varian 390-LC-Multi detector suite fitted with differential refractive index (DRI), light scattering (LS), and ultraviolet (UV) detectors equipped with a guard column (Varian Polymer Laboratories PLGel 5 µM, 50×7.5 mm) and two mixed D columns (Varian Polymer Laboratories PLGel 5 µM, 300×7.5 mm). The mobile phase was either tetrahydrofuran eluent or tetrahydrofuran with 5% triethylamine eluent at a flow rate of 1.0 mL·min$^{-1}$, and samples were calibrated against Varian Polymer Laboratories Easi-Vials linear poly(styrene) standards (162–3.7×10$^5$ g mol$^{-1}$) using Cirrus v3. The dymamic light scattering (DLS) measurements were performed by Mr Jerry Cabiness fromNanosight Inc. and were measured in $CH_2Cl_2$ as solvent.

Samples for transmission electron microscopy (TEM) imaging were prepared by dissolving 0.5 mg nanoparticles in a solution of 1 mL isopropanol, 0.3 mL acetonitrile and 0.2 mL toluene. The samples were sonicated for 5 min and stained with 3 drops of 3% phosphotungstic acid. The carbon grids were prepared by slowly dipping an Ultrathin Carbon Type-A 400 Mesh Copper Grid (Ted Pella, Inc., Redding, Calif.) into the particle solution three times and air drying the grid at room temperature. A Philips CM20T transmission electron microscope operating at 200 kV in bright-field mode was used to obtain TEM micrographs of the polymeric nanoparticles.

(b) General Procedure for Ring-Opening Polymerization

Polymerizations were completed in glovebox. A solution of ethyl 5-methyl-2-oxo-1,3-dioxane-5-carboxylate (397 mg, 2.112 mmol) and allyl 5-methyl-2-oxo-1,3-dioxane-5-carboxylate (106 mg, 0.528 mmol) in $CH_2Cl_2$ (0.84 mL) was added to a stirred solution of 1-(3,5-bis(trifluoromethyl)phenyl)-3-cyclohexylthiourea (97.8 mg, 0.264 mmol), benzyl alcohol (13.7 µL, 0.132 mmol) and sparteine (30.3 µL, 0.132 mmol) in $CH_2Cl_2$ (0.84 mL). After the allotted period of time, the reaction was twice precipitated from $CH_2Cl_2$ into hexanes and dried under reduced pressure. Residual catalyst impurities were removed by column chromatography on silica (80% hexanes, 20% ethyl acetate). Purified polymer was dried under reduced pressure. $^1H$ NMR (400 MHz, $CDCl_3$/TMS, ppm) $\delta$: 7.37 (m, OBn-ArH), 5.9 (m, $CH_{vinyl}$), 5.3 (m, $CH_{2-vinyl}$), 5.15 (s, OBn-$CH_2$), 4.64 (m, $OCH_2CHCH_2$), 4.40-4.18 (m, MAC & MTC-et, OC(O) $OCH_2$), 1.30-1.22 (m, MAC, $CH_3$; MTC-et, $OCH_2CH_3$)

(c) General Procedure for Oxidation of Copolymers

3-Chloroperoxybenzoic acid (30.4 mg, 0.176 mmol) was added to a stirred solution of poly(MTC-Et, MTC-allyl) (0.200 g, 0.214 mmol) in $CH_2Cl_2$ (3.7 mL). The mixture stirred for 48 hours at room temperature. Residual 3-chloroperoxybenzoic acid was removed by dialysis against dichloromethane using Spectra/Por Dialysis Membrane (MWCO=2,000) to yield pure polymer (0.180 g). $^1H$ NMR (400 MHz, $CDCl_3$/TMS, ppm) $\delta$: The significant change is the disappearance of the allylic protons at 5.9 and 5.3 ppm and the emergence of small broad peaks at 3.19, 2.82, and 2.63 ppm due to formation of the epoxide ring.

(d) Nanoparticle Formation:

Poly(5% MTC-allyl, 95% MTC-et) nanoparticle formation using thiol-ene cross-linking with 3,6-dioxa-1,8-octanedithiol 3,6-dioxa-1,8-octane-dithiol (18.4 µL, 0.113 mmol) was added to a solution of poly(5% MTC-allyl, 95% MTC-Et) (100 mg, $M_n$=5.0 kDa, PDI=1.56) in $CH_2Cl_2$ (8.7 mL). The reaction mixture refluxed for 12 hours at 45° C. Residual cross-linker was removed by dialyzing with SnakeSkin Pleated Dialysis Tubing (MWCO=10,000) against $CH_2Cl_2$ to yield particles (96 mg). $^1H$ NMR (400 MHz, $CDCl_3$/TMS, ppm) $\delta$: The significant change is the disappearance of the allylic protons at 5.9 and 5.3 ppm and the emergence of peaks at 3.64 ppm due to the methylene protons adjacent to the oxygens in the crosslinker and 2.73-2.68 ppm due to methylene protons adjacent to the sulfide functionality.

b. Discussion

Functionalized linear polycarbonates prepared using organocatalytic synthesis and $Sn(OTf)_2$ metal catalyzed methods where further post-modified via thiolene-click reactions and epoxide-amine reactions to form nanoparticles by an intermolecular cross-linking approaches.

Value-driven engineering and the synthesis of biomaterials for applications in tissue engineering, wound healing and drug delivery is one of the driving forces in the development of defined and functionalized materials. While the preparation of poly(ester) and poly(carbonate) based particles has been mainly driven by precipitation processes, chemically driven nanoparticle synthesis has given the opportunity to control sizes and architectural nature of the particles. Especially intramolecular[1,2] and inter chain-crosslinking processes[3,4] have shown to be useful routes. Some of us have demonstrated that the intermolecular chain cross-linking of side-chain functional poly(ester)s derived by ring-opening polymerization of substituted δ-valerolactone monomers provides a facile methodology for versatile nanoparticle preparation.[5-8] This methodology affords controlled nanoparticle sizes that can be varied via the percentiles of side-chain functionalities into the linear polyester precursor. Furthermore, the morphology and size can be controlled with the amount of difunctionalized cross-linking units, reacting with the side-chain functionality of the polymer. With this, functionalized particles that are further post-modified to react with targeting units and turned into drug delivery systems upon encapsulation can be tested for their biological response.[8,9]

Herein we demonstrate that for the first time, allyl- and epoxide-functional aliphatic poly(carbonate)s can be applied in the intramolecular chain crosslinking process for the synthesis of poly(carbonate) nanosponges (FIG. 1).

Extension of the organocatalytic methods for ROP of 5-methyl-5-allyloxycarbonyl-1,3-dioxane-2-one (MAC) to prepare copolymers with 5-methyl-5-ethyloxycarbonyl-1,3-dioxane-2-one (MTC-Et) to provide lower functional group densities was undertaken.[21] With this approach, the allyl functionalities are, for example, excellent groups with which to form particles in intermolecular chain cross-linking reactions and other post-modifications using thiol-ene click chemistry. Furthermore, as previously demonstrated by Storey and co-workers,[22] the oxidation of allyl-functional poly(carbonate)s with m-CPBA results in the formation of the epoxide-functional polymers to provide an alternative group that has been proven to be very valuable to the synthesis of nanoparticles and functionalization reactions in surface labeling. Our initial studies focused on the synthesis of a range of copolymers of MAC and MTC-Et cyclic carbonate monomers with different incorporations of MAC using the previously optimized ROP conditions for MAC homopolymerization.[22] To this end, a series of copolymers with increasing amounts of MAC to MTC-Et were prepared (Table 1) initiated from benzyl alcohol using the (−)— sparteine/thiourea catalyst system (Scheme 1).

In another appraoch to circumvent complicated glove box procedures associated with systems that are catalyzed with organo catalysts, we have found a practical approach to facilitate well-controlled polycarbonate polymers with use of $Sn(OTf)_2$. The Sn endgroup can be removed by quenching the reaction with MeOH.

Scheme 1. Synthesis of Polycarbonate Copolymers with 5%, 10% and 20% incorporation of MAC and subsequently oxidation of the allyl to the pendant epoxide group

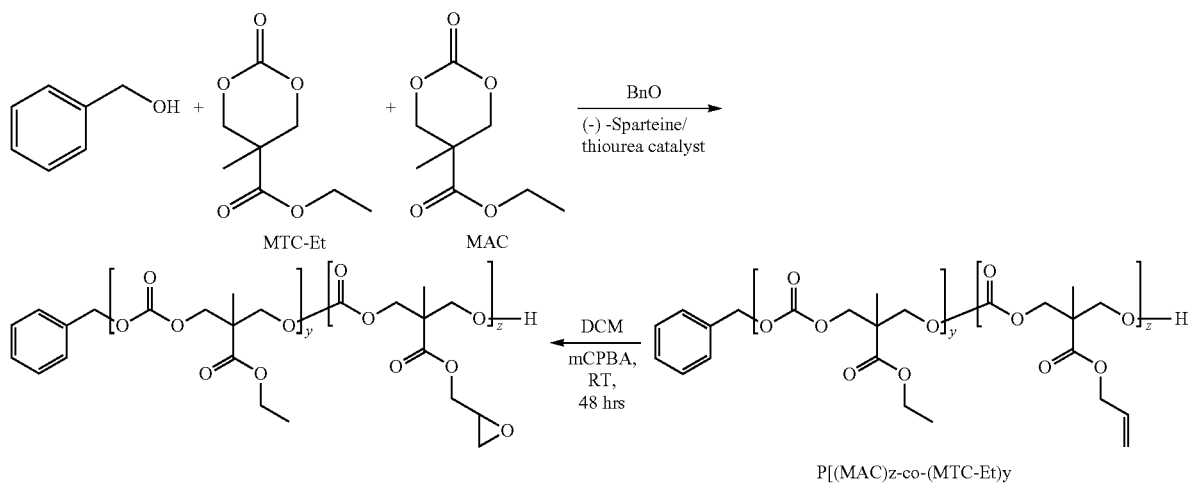

The observed copolymers showed a good control in molecular weight although slightly broad dispersities that are a consequence of high molecular weight tailing of the polymer distributions (see Supporting Information). Incorporation of the MAC monomer, which contains the allyl-functionality, was consistent with the monomer feed ratios as confirmed by $^1H$ NMR spectrscopy. The ability of the copolymers (Table 1) to form nanoparticles was investigated via the previously developed thiol-ene "click" chemistry and epoxide-amine reaction.

TABLE 1

Ring-opening copolymerization of MAC and MTC ([a]All polymerizations were conducted in dichloromethane at 25° C., [monomer] = 1.6M, [monomer]/[initiator] = 20 using benzyl alcohol as initiator with 10 mol % TU and 5 mol % (−)-sparteine as catalysts. Molecular weight and polydispersity were determined using GPC calibrated with poly(styrene) standards in chloroform. Conversion and molecular weight were determined by NMR.)

| Polymer Composition (MTC-Et:MAC) | Monomer Conversion (%) | $M_n$(GPC) (KDa) | $M^n$(NMR) (KDa) | PDI |
|---|---|---|---|---|
| 95:5 | >95 | 4.7 | 5.0 | 1.56 |
| 90:10 | >95 | 5.0 | 5.3 | 1.25 |
| 80:20 | >95 | 4.9 | 6.4 | 1.39 |

The Reaction of 8 equivalents of the dithiolethylenoxide cross-linker to the P[(MAC)$_z$-co-(MTC-Et)$_y$] functionalized polymer containing 5%, 10% and 20% MAC and the allyl functionality led to the observation of well-defined poly(carbonate) nanosponges (Supporting Information). TEM and DLS analysis showed that the increasing amount of cross-linker in the polymer backbone led to larger particle that displayed number-average solution hydrodynamic diameters, $D_h$ of ~220 nm for the 20% cross-linker-containing particles, in contrast to smaller particle sizes of $D_h$=150 nm for the particles prepared with 5% MAC comonomer incorporated. The DLS data suggested that the higher cross-linking led also to a higher degree of particle deviation (FIG. 2). In comparison to thiolene-"click" reactions with analogous poly(ester) linear polymers, the poly(carbonate)-derived particles are smaller than expected, attributed to a lower degree of polymerization of the poly(carbonate) copolymers than those reported from the poly(ester) polymers and its analogs.

As an alternative methodology, particle formation using epoxide-amine cross-linking chemistry, analogous to the functionalized poly(ester) particles, was investigated. The MAC-containing copolymers were fully epoxidized by treatment with 1.2 eq. mCPBA in CH$_2$Cl$_2$ to form the suitable linear precursor. The disappearance of the characteristic vinyl resonances in the range δ=5.9-5.3 ppm was observed with the appearance of resonances that are clearly attributable to the formation of epoxide-functional polymers at δ=3.19, 2.82, and 2.63 ppm (Supporting Information). Other resonances in the $^1$H NMR spectrum of the polymers did not change and the same chain length was determined by end group analysis.

Reaction of the functionalized copolymers containing 5%, 10% and 20% epoxide pendant functional groups with also 8 eq. diaminoethyleneoxide was performed to intermolecularly crosslink the polymers (Supporting Information). Analysis of the resultant nanosponges, again via $^1$H-NMR spectroscopy, TEM and DLS, demonstrated that particles slightly increased sizes of $D_h$=230 nm for the particles with 20% cross-linking in contrast to $D_h$=160 nm for particles prepared from the lowest cross-linking density available in the study (FIG. 2). In comparison to analogouspoly(ester) materials, the particle sizes are smaller, again attributed to the lower degree of polymerization in contrast to the previously investigated polyester materials.

In summary, we have prepared functionalized poly(carbonate) copolymers of 5-methyl-5-allyl-oxycarbonyl-1,3-dioxan-2-one (MAC) and 5-Methyl-5-ethyloxycarbonyl-1,3-dioxane-2-one (MTC-Et) via organocatalytic synthesis under mild conditions using a thiourea and (−)-sparteine catalyst system. The pendant allyl groups were utilized as cross-linking partners in thiol-ene click reactions forming nanosponges in the sizes of 150-220 nm depending on the cross-linking density of the linear precursor with 5%, 10% and 20% of pendant allyl groups incorporated. The oxidation of the allyl groups in the copolymers to epoxides was successful and the following cross-linking reaction with diaminesenabled the synthesis of thenanosponge particles in size ranges of 160-230 nm using an alternative epoxide-amine chemistry. For the first time we have demonstrated the formation of functionalized poly(carbonate) particles with the established intermolecular cross-linking process.

c. Ethyl Carbonate Homopolymer Synthesis
(a) Synthesis of Ethyl Polycarbonate Homopolymer

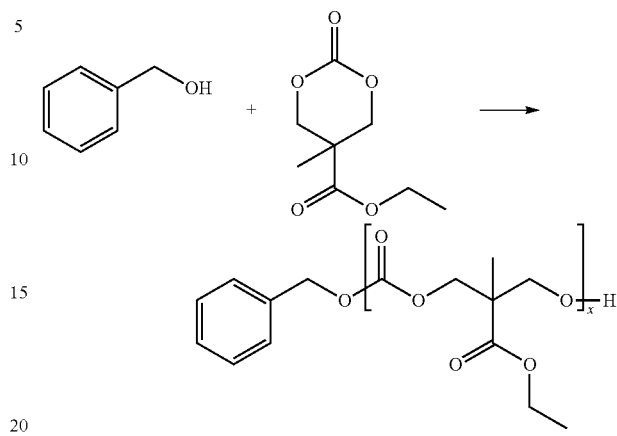

Added MTC-Et (100 mg, 0.531 mmol), Sn(OTf)$_2$ (5 uL, 0.037 M in THF), and benzyl alcohol (14.7 uL, 1.7 M in THF) to a nitrogen-purged, flame-dried 25-mL round bottom flask. Two additional milliliters of dry THF were added to dissolve everything. Reaction stirred at room temperature for 48 hours. NO RXN (b) Synthesis of Ethyl Polycarbonate Homopolymer ([mon]:[cat]:[init]=1250:1:50)

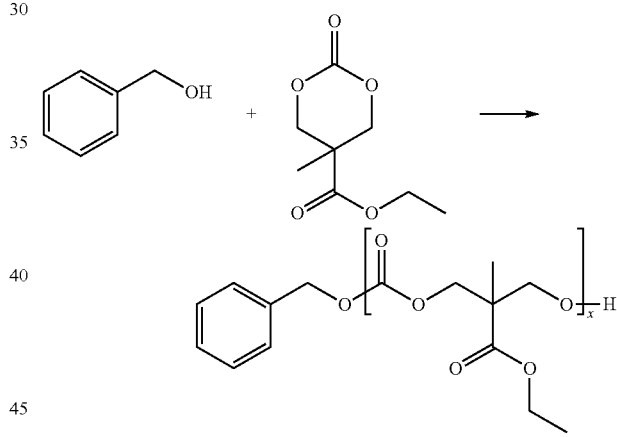

A 1-dram vial was equipped with stir bar, capped with rubber septum, flame dried and nitrogen purged. MTC-Et (0.500 g, 2.660 mmol) and Sn(OTf)$_2$ (0.89 mg, 0.0213 mmol) were added to the vial, and the vial was nitrogen purged once more. The vial was added to 65° C. oil bath and allowed to stir for 5 minutes before adding the benzyl alcohol (11 uL, 0.106 mmol) and allowing to stir at 65° C. overnight to yield polymer next morning.

(C) Synthesis of Ethyl Polycarbonate Homopolymer ([mon]:[cat]:[init]=1250:1:50)

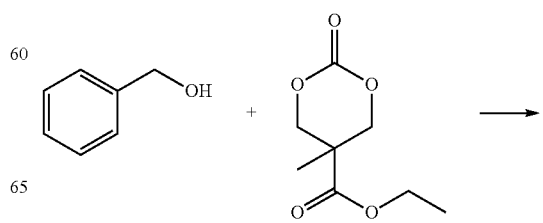

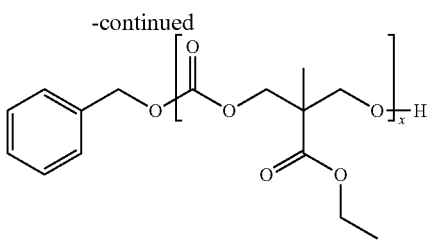

Added Sn(OTf)$_2$ (57.5 uL, 0.037 M in THF) and benzyl alcohol (62.6 uL, 1.7 M in THF) to a nitrogen-purged, flame-dried 25-mL round bottom flask. The catalyst/initiator mixture was allowed to stir at room temperature for several minutes before adding MTC-Et (500 mg, 2.660 mmol). An additional 500 uL dry THF was required to dissolve all reagents. Reaction stirred at room temperature for 5 days. Reaction was quenched by adding dichloromethane and hexanoic acid. The polymer was purified by crashing out in hexanes to yield polymer (PDI=1.11).

d. Ethyl Carbonate Homopolymer Kinetics

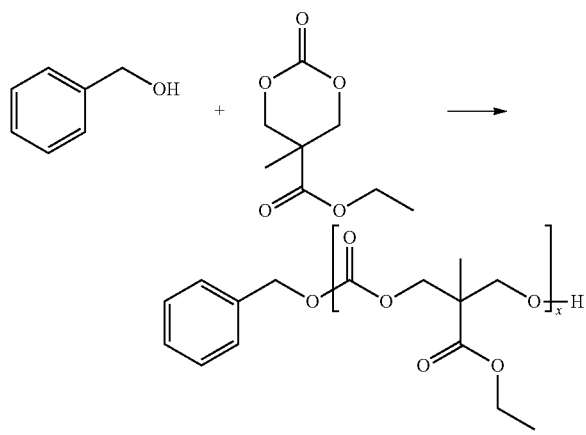

([mon]:[cat]:[init]=1250:1:50)

Figure 3:
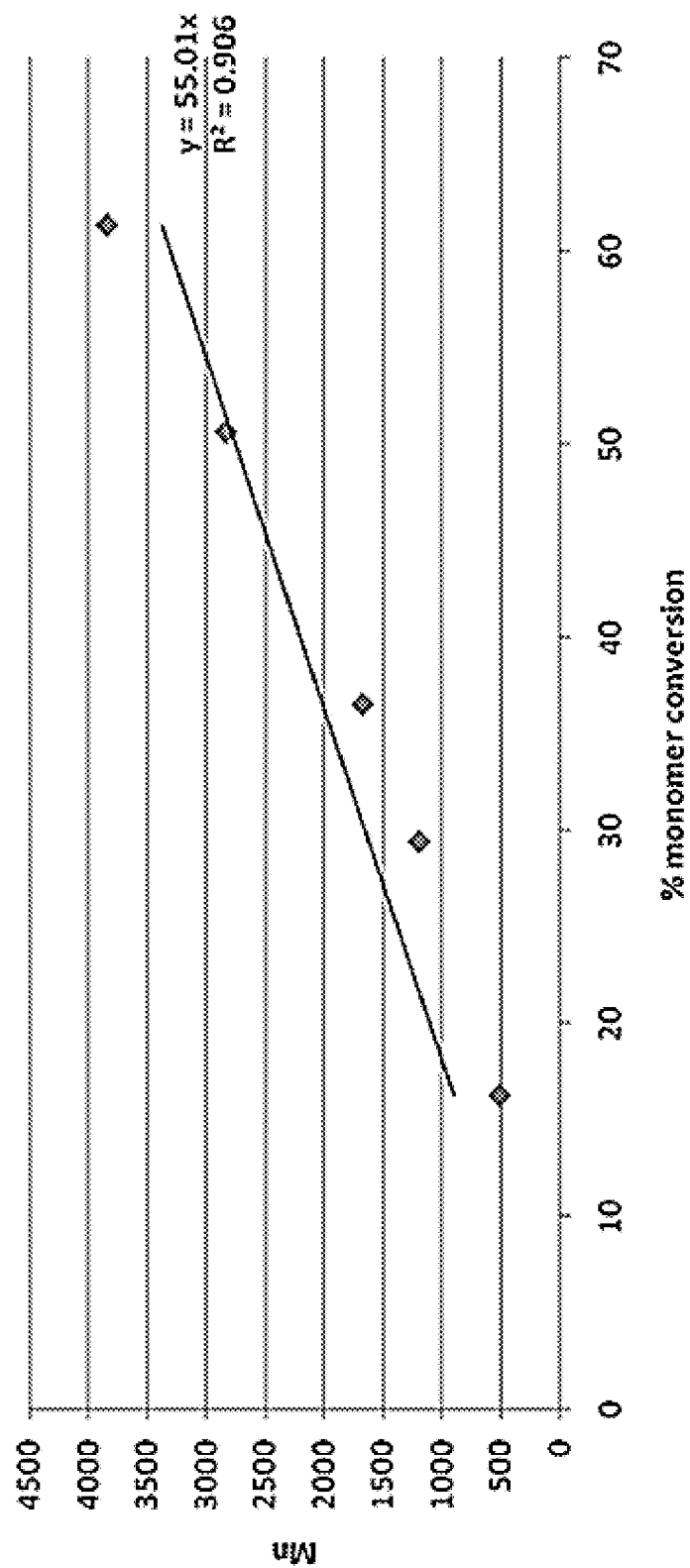
FIG. 3 shows the results for the kinetic results for ethyl carbonate homopolymers.

A 1-dram vial was equipped with stir bar, capped with septum, flame dried, and nitrogen purged. Sn(OTf)$_2$ (0.17 mL, 0.0124 M in ethyl acetate) and benzyl alcohol (0.17 mL, 0.611 M in ethyl acetate) were added to the vial via syringe, and ethyl acetate was evaporated off via nitrogen flow. MTC-Et (500 mg, 2.660 mmol) was added and allowed to stir at 70° C. At each time point, a small amount of the reaction was removed via syringe and analyzed by NMR. The results for the kinetics for ethyl carbonate homopolymers can be seen in FIG. 3.

e. Kinetics of Poly(MTC-Et) ([MON]:[CAT]:[INIT]=1250:4:50)

Figure 4:
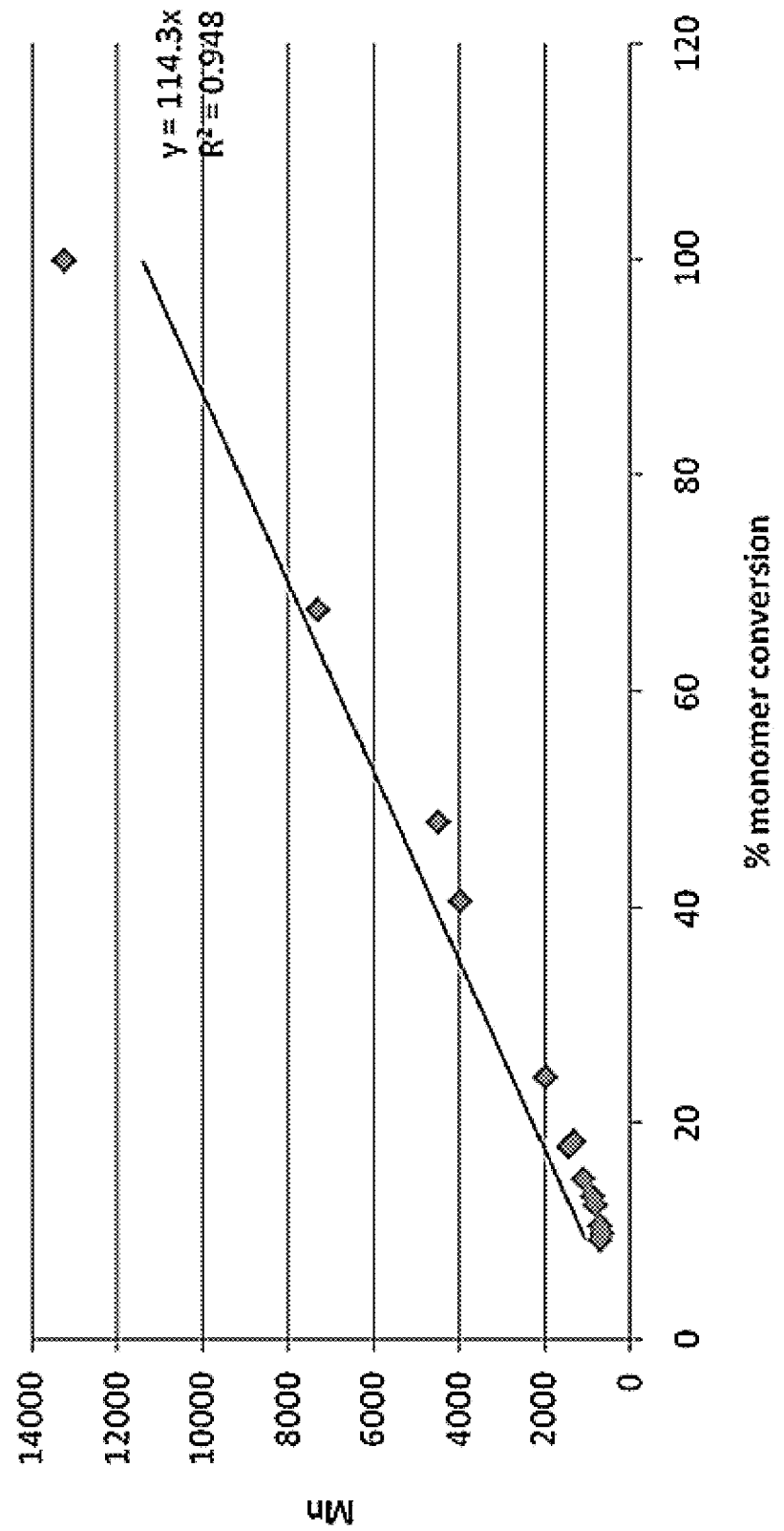
FIG. 4 shows the results for the kinetic results for poly (MTC-Et) having a [mon]:[cat]:[init] ration of 1250:4:50.

A 25 mL round bottom flask was equipped with a stir bar, capped with a rubber septum, argon purged and flame dried. Sn(OTf)$_2$ (7.5 mg, 0.018 mmol) was weighed directly into the flask followed by the addition of MTC-Et (1.00 g, 5.319 mmol). The flask was sealed with rubber septum, argon purged and set to stir in a 70° C. oil bath. Benzyl alcohol (22 uL, 0.210 mmol) was added to the flask via microsyringe. At each time point, a small amount of the reaction was removed via syringe and analyzed by NMR. The results for the kinetics of poly(MTC-Et) having a [mon]:[cat]:[init] ration of 1250:4:50 can be seen in FIG. 4.

f. Kinetics of Poly(MTC-Et) ([MON]:[CAT]:[INIT]=1250:10:50)

Figure 5:
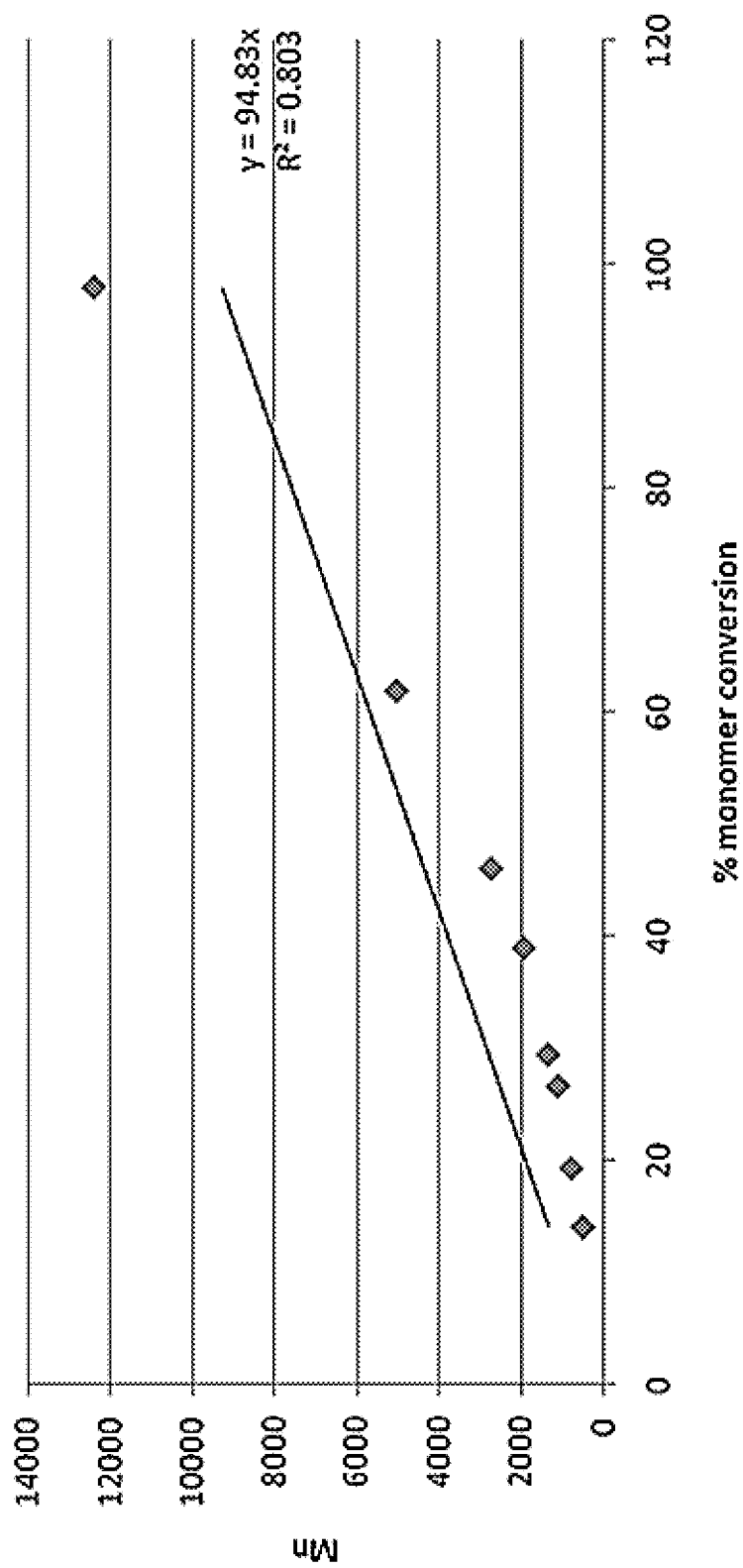
FIG. 5 shows the results for the kinetic results for poly (MTC-Et) having a[mon]:[cat]:[init] ration of 1250:10:50.

A 25 mL round bottom flask was equipped with a stir bar, capped with a rubber septum, argon purged and flame dried. Sn(OTf)$_2$ (17.7 mg, 0.042 mmol) was weighed directly into the flask followed by the addition of MTC-Et (1.00 g, 5.319 mmol). The flask was sealed with rubber septum, argon purged and set to stir in a 70° C. oil bath. Benzyl alcohol (22 uL, 0.210 mmol) was added to the flask via microsyringe. At each time point, a small amount of the reaction was removed via syringe and analyzed by NMR. The results for the kinetics of poly(MTC-Et) having a[mon]:[cat]:[init] ration of 1250:10:50 can be seen in FIG. 5.

g. Kinetics of Poly(MTC-Et) ([MON]:[CAT]:[INIT]=1250:4:50)

Figure 6:
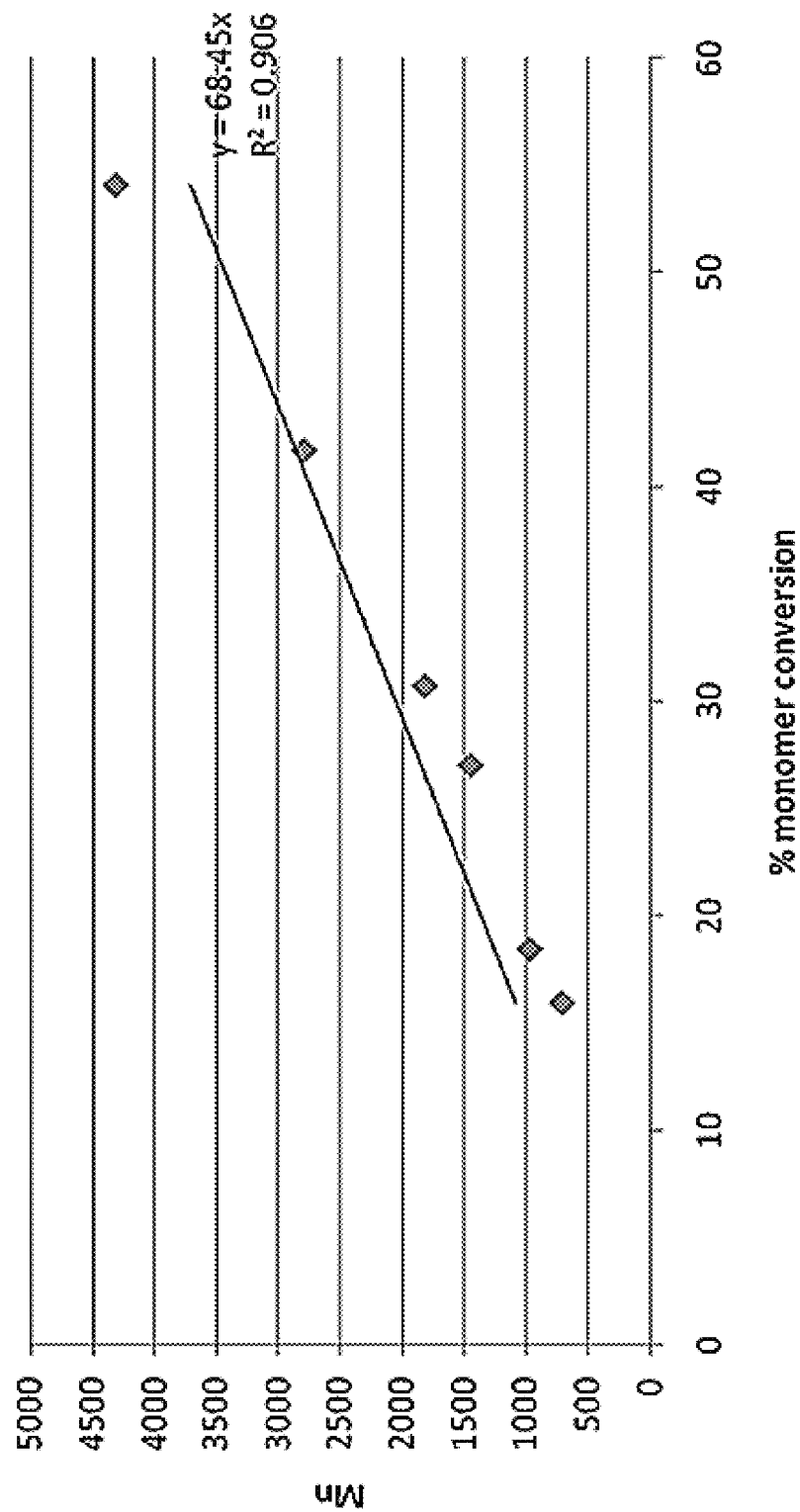
FIG. 6 shows the results for the kinetic results for poly (MTC-Et) having a [mon]:[cat]:[init] ration of 1250:4:50.

A 25 mL round bottom flask was equipped with a stir bar, capped with a rubber septum, argon purged and flame dried. Sn(OTf)$_2$ (7.5 mg, 0.018 mmol) was weighed directly into the flask followed by the addition of MTC-Et (1.00 g, 5.319 mmol). The flask was sealed with rubber septum, argon purged and set to stir in a 70° C. oil bath. Benzyl alcohol (22 uL, 0.210 mmol) was added to the flask via microsyringe. At each time point, a small amount of the reaction was removed via syringe and analyzed by NMR. The results for the kinetics of poly(MTC-Et) having a [mon]:[cat]:[init] ration of 1250:4:50 can be seen in FIG. 6.

h. Kinetics of Poly(MTC-Et) ([MON]:[CAT]:[INIT]=1250:10:50)

Figure 7:
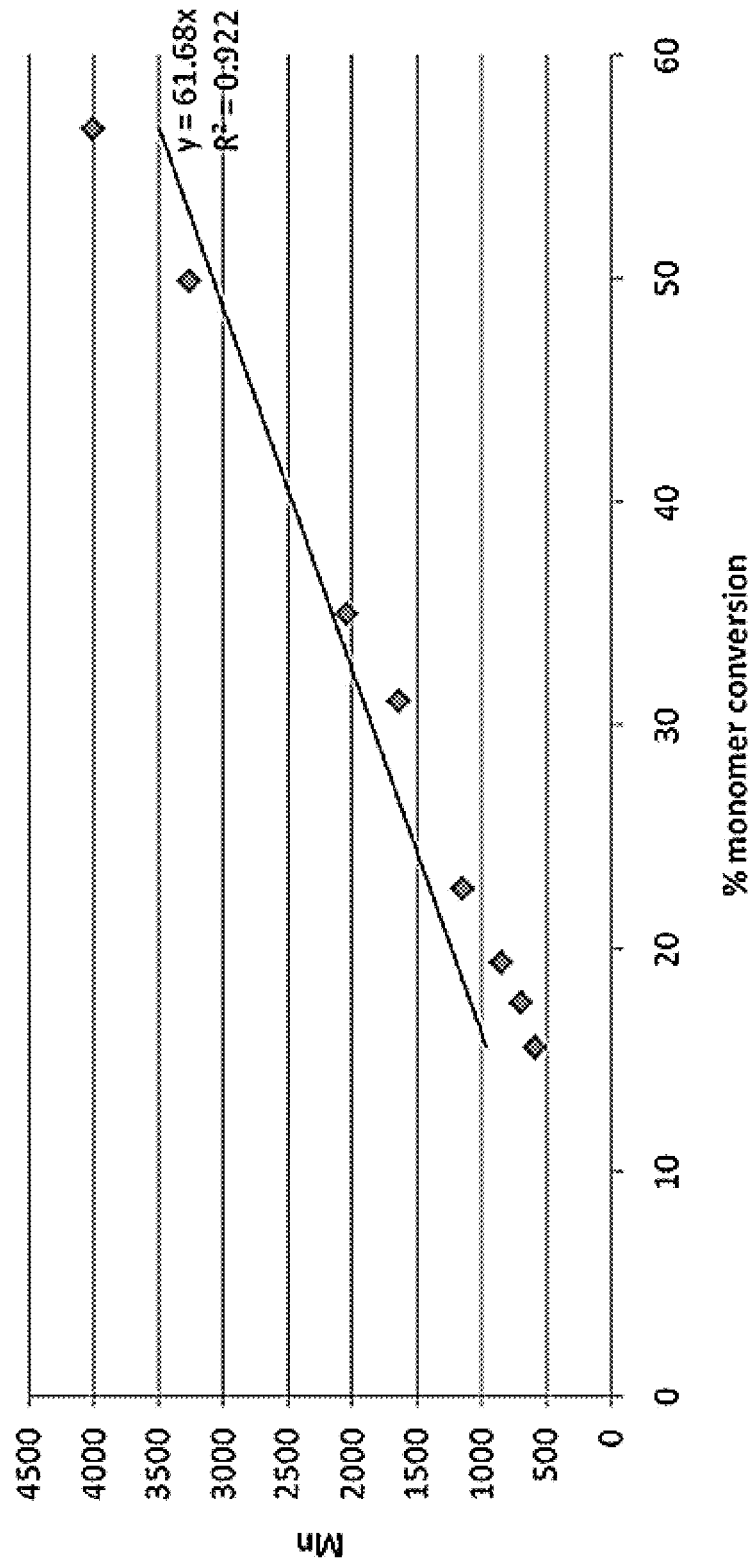
FIG. 7 shows the results for the kinetic results for poly (MTC-Et) having a[mon]:[cat]:[init] ration of 1250:10:50.

A 25 mL round bottom flask was equipped with a stir bar, capped with a rubber septum, argon purged and flame dried. Sn(OTf)$_2$ (17.7 mg, 0.042 mmol) was weighed directly into the flask followed by the addition of MTC-Et (1.00 g, 5.319 mmol). The flask was sealed with rubber septum, argon purged and set to stir in a 70° C. oil bath. Benzyl alcohol (22 uL, 0.210 mmol) was added to the flask via microsyringe. At each time point, a small amount of the reaction was removed via syringe and analyzed by NMR. The results for the kinetics of poly(MTC-Et) having a[mon]:[cat]:[init] ration of 1250:10:50 can be seen in FIG. 7.

i. Kinetics of Poly(MTC-Et) ([MON]:[CAT]:[INIT]=1250:4:50)

Figure 8:
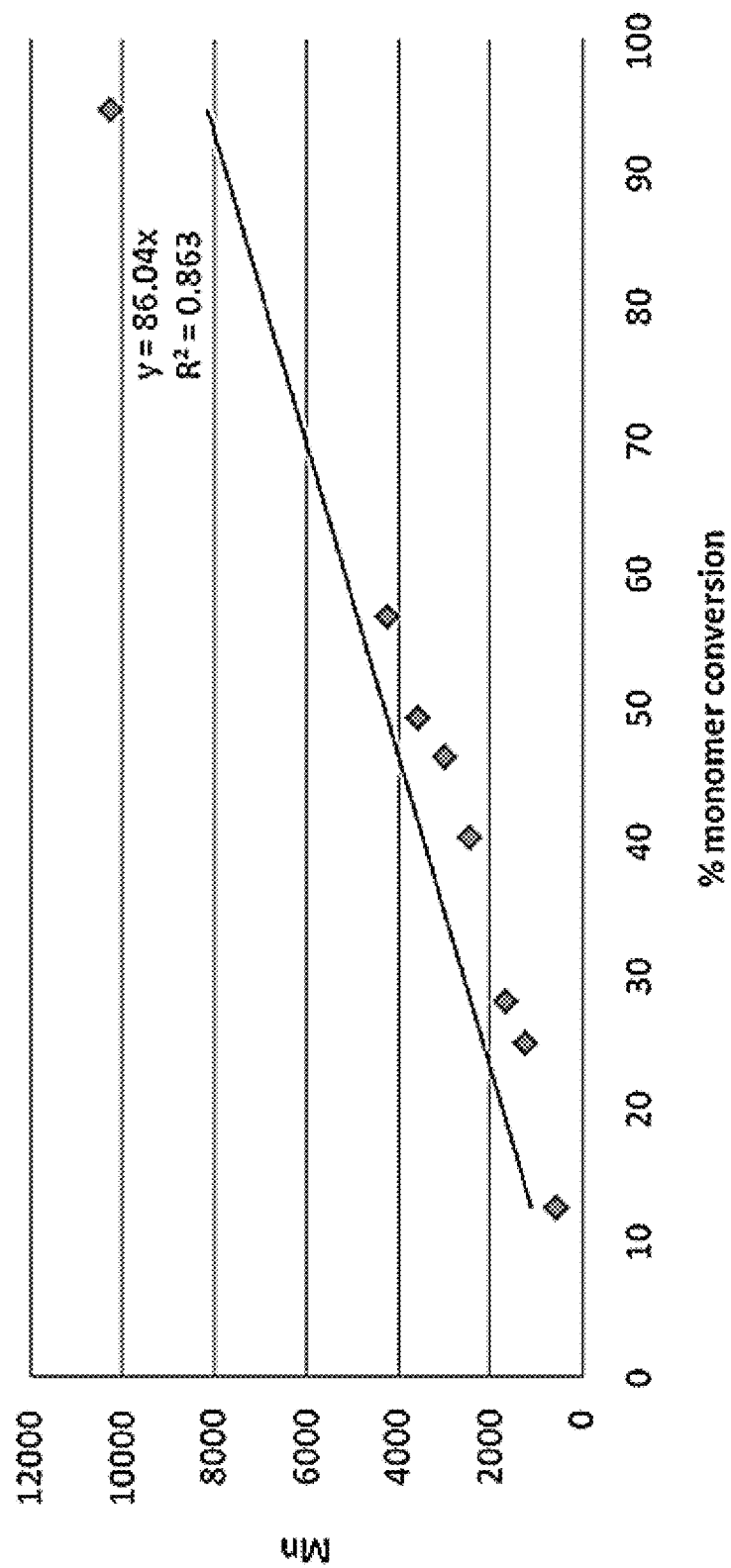
FIG. 8 shows the results for the kinetic results for poly (MTC-Et) having a [mon]:[cat]:[init] ration of 1250:4:50.

A 25 mL round bottom flask was equipped with a stir bar, capped with a rubber septum, argon purged and flame dried. Sn(OTf)$_2$ (6.8 mg, 0.016 mmol) was weighed directly into the flask. The flask was sealed with rubber septum, argon purged and set to stir in a 70° C. oil bath. Benzyl alcohol (22 uL, 0.210 mmol) was added to the flask via microsyringe and the catalyst/iniator solution was allowed to stir at 70° C. for 30 minutes. MTC-Et (1.00 g, 5.319 mmol) was added to the solution and allowed to stir. At each time point, a small amount of the reaction was removed via syringe and analyzed by NMR. The results for the kinetics of poly(MTC-Et) having a [mon]:[cat]:[init] ration of 1250:4:50 can be seen in FIG. 8.

j. Synthesis of Carbonate Copolymers (a) Synthesis of Poly(20% MTC-allyl, 80% MTC-Et) ([MON]:[CAT]:[INIT]=1250:1:50)
([mon]:[cat]:[init]=1250:1:50)

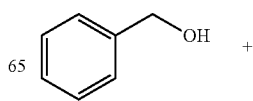

(c) Synthesis of Poly(20% MTC-allyl, 80% MTC-Et) ([MON]:[CAT]:[INIT]=1250:1:50)

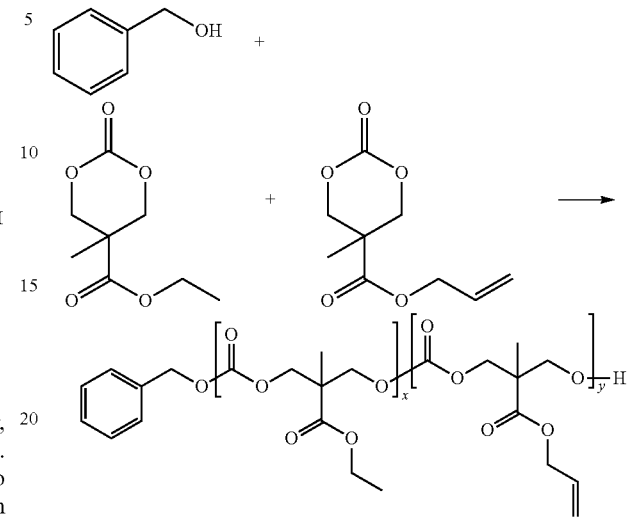

A 1-dram vial was equipped with stir bar, capped with septum, flame dried, and nitrogen purged. Sn(OTf)$_2$ (0.17 mL, 0.0124 M in ethyl acetate) and benzyl alcohol (0.17 mL, 0.611 M in ethyl acetate) were added to the vial via syringe, and ethyl acetate was evaporated off via nitrogen flow. MTC-allyl (105 mg, 0.525 mmol) and MTC-Et (395 mg, 2.101 mmol) were added and allowed to stir at 80° C. for a week. NO RXN (d) Synthesis of Poly(20% MTC-allyl, 80% MTC-Et) ([MON]:[CAT]:[INIT]=1250:2:50)

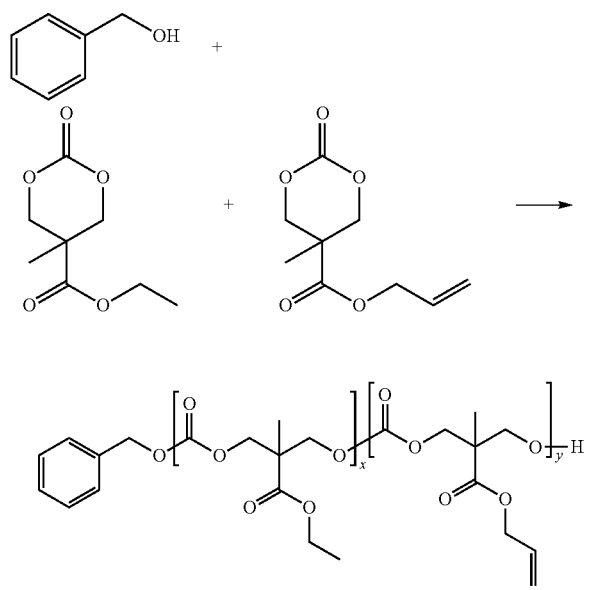

A 1-dram vial was equipped with stir bar, capped with septum, flame dried, and nitrogen purged. Sn(OTf)$_2$ (0.34 mL, 0.0124 M in ethyl acetate) and benzyl alcohol (0.17 mL, 0.611 M in ethyl acetate) were added to the vial via syringe, and ethyl acetate was evaporated off via nitrogen flow. MTC-allyl (105 mg, 0.525 mmol) and MTC-Et (395 mg, 2.101 mmol) were added and allowed to stir at 70° C. for a week. Crashed out in hexanes to yield polymer (~40% conversion, PDI=1.08).

-continued

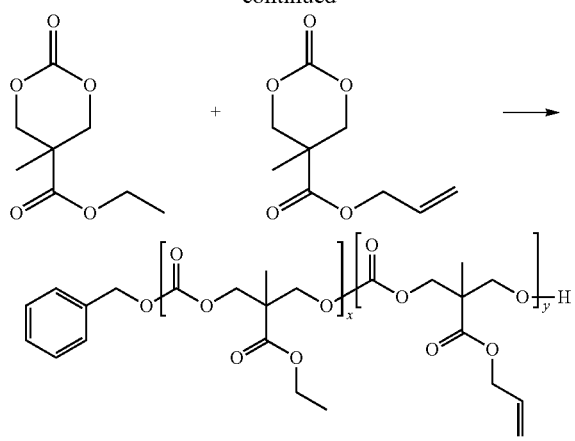

A 25 mL round bottom flask was equipped with a stir bar, capped with a rubber septum, argon purged and flame dried. Sn(OTf)$_2$ (0.88 mg, 0.0213 mmol) was weighed directly into the flask. The flask was sealed with rubber septum, argon purged and set to stir in a 65° C. oil bath. Benzyl alcohol (11 uL, 0.105 mmol) was added to the flask via microsyringe and allowed to stir for 5 minutes. MTC-allyl (105 mg, 0.525 mmol) and MTC-Et (395 mg, 2.101 mmol) were added directly to the flask and it was re-capped with septum and purged again with argon. The reaction was allowed to stir at 65° C. for several days. NO RXN (b) Synthesis of Poly(20% MTC-allyl, 80% MTC-Et) ([MON]:[CAT]:[INIT]=1250:1:50)

A 1-dram vial was equipped with stir bar, capped with septum, flame dried, and nitrogen purged. Sn(OTf)$_2$ (0.17 mL, 0.0124 M in ethyl acetate) and benzyl alcohol (0.17 mL, 0.611 M in ethyl acetate) were added to the vial via syringe, and ethyl acetate was evaporated off via nitrogen flow. MTC-allyl (105 mg, 0.525 mmol) and MTC-Et (395 mg, 2.101 mmol) were added and allowed to stir at 70° C. for a week. NO RXN (e) Synthesis of Poly(20% MTC-allyl, 80% MTC-Et) ([MON]:[CAT]:[INIT]=1250:3:50)

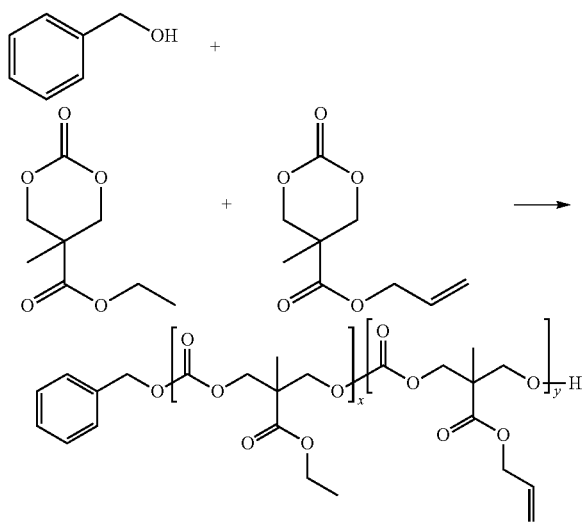

A 1-dram vial was equipped with stir bar, capped with septum, flame dried, and nitrogen purged. Sn(OTf)$_2$ (0.34 mL, 0.0124 M in ethyl acetate) and benzyl alcohol (0.17 mL, 0.611 M in ethyl acetate) were added to the vial via syringe, and ethyl acetate was evaporated off via nitrogen flow. MTC-allyl (105 mg, 0.525 mmol) and MTC-Et (395 mg, 2.101 mmol) were added and allowed to stir at 70° C. for 4 days.

(f) Synthesis of Poly(20% MTC-allyl, 80% MTC-Et) ([MON]:[CAT]:[INIT]=1250:4:50)

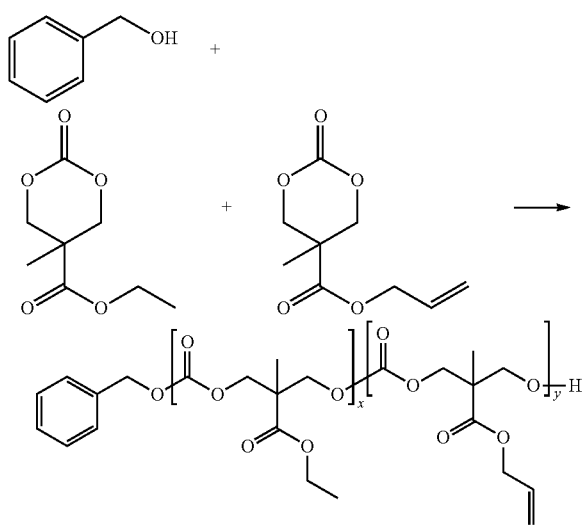

A 1-dram vial was equipped with stir bar, capped with septum, flame dried, and nitrogen purged. Sn(OTf)$_2$ (0.68 mL, 0.0124 M in ethyl acetate) and benzyl alcohol (0.17 mL, 0.611 M in ethyl acetate) were added to the vial via syringe, and ethyl acetate was evaporated off via nitrogen flow. MTC-allyl (105 mg, 0.525 mmol) and MTC-Et (395 mg, 2.101 mmol) were added and allowed to stir at 70° C. for 3 days.

(g) Synthesis of Poly(20% MTC-allyl, 80% MTC-Et) ([MON]:[CAT]:[INIT]=1250:1:50)

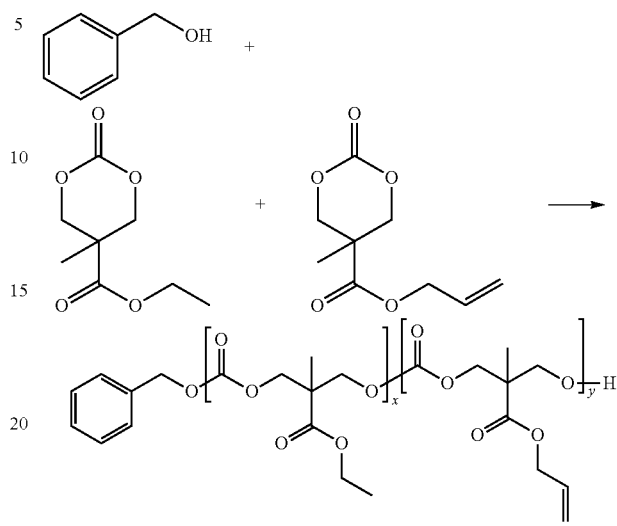

A 1-dram vial was equipped with stir bar, capped with septum, flame dried, and nitrogen purged. Sn(OTf)$_2$ (0.17 mL, 0.0124 M in ethyl acetate) and benzyl alcohol (0.17 mL, 0.611 M in ethyl acetate) were added to the vial via syringe, and ethyl acetate was evaporated off via nitrogen flow. MTC-allyl (105 mg, 0.525 mmol) and MTC-Et (395 mg, 2.101 mmol) were added and allowed to stir at 90° C. for a week. NO RXN (h) Synthesis of Poly(20% MTC-allyl, 80% MTC-Et) ([MON]:[CAT]:[INIT]=1250:10.6:50)

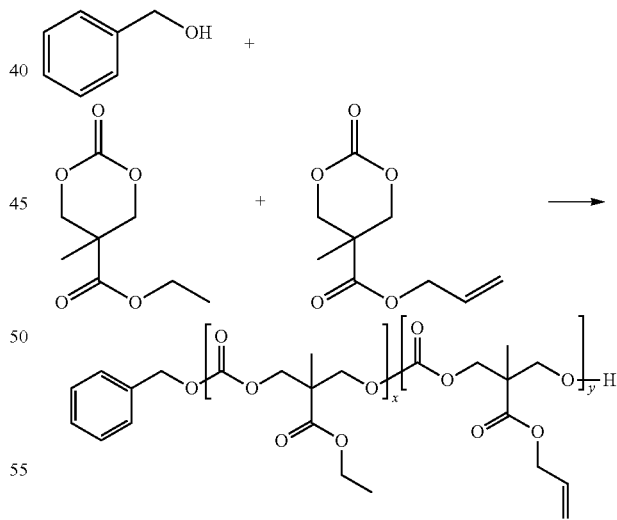

A 25 mL round bottom flask was equipped with a stir bar, capped with a rubber septum, argon purged and flame dried. Sn(OTf)$_2$ (18.5 mg, 0.044 mmol) was weighed directly into the flask. The flask was sealed with rubber septum, argon purged and set to stir in a 70° C. oil bath. Benzyl alcohol (22 uL, 0.210 mmol) was added to the flask via microsyringe and allowed to stir for 5 minutes. MTC-allyl (210 mg, 1.050 mmol) and MTC-Et (790 mg, 4.202 mmol) were added directly to the flask and it was re-capped with septum and purged again with argon. The reaction was allowed to stir at 70° C. overnight. To quench the reaction, methanol was added and residual monomers were removed by crashing out the polymer in a vortexing solution of hexanes two times to yield slightly off-white polymer (0.791 g, NMR Mn=6095, 18.1% allyl, 81.9% ethyl).

(i) Synthesis of Poly(20% MTC-allyl, 80% MTC-Et) ([MON]:[CAT]:[INIT]=1250:4:50)

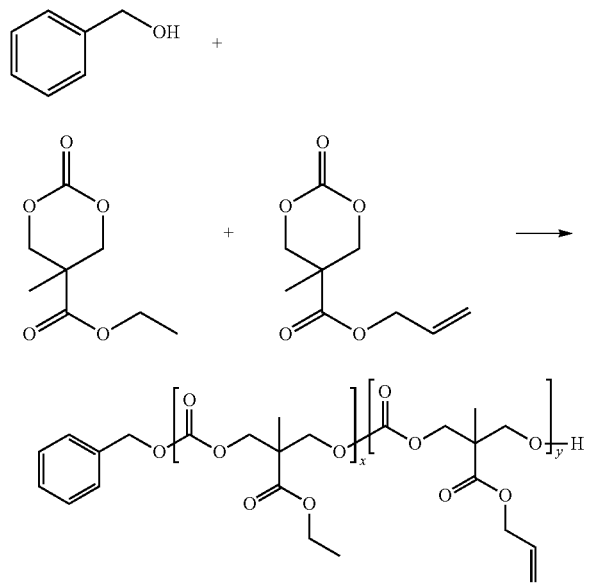

Procedure same as described elsewhere herein with the difference being that 7.0 mg Sn(OTf)$_2$ was used (0.017 mmol). Reaction took ~90 hours (NMR Mn=4,887, 82.2% ethyl, 17.8% allyl).

(j) Synthesis of Poly(20% MTC-allyl, 80% MTC-Et) ([MON]:[CAT]:[INIT]=1250:4:50)

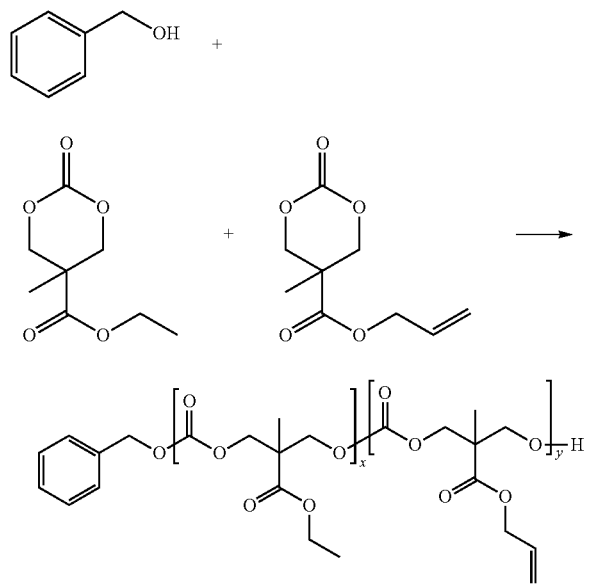

A 25 mL round bottom flask was equipped with a stir bar, capped with a rubber septum, argon purged and flame dried. Sn(OTf)$_2$ (8.0 mg, 0.0192 mmol) was weighed directly into the flask, capped with septum, and argon purged again. Benzyl alcohol (22 uL, 0.210 mmol) was added to the flask via microsyringe and allowed to stir in 70° C. oil bath for 30 minutes. MTC-Et (790 mg, 4.202 mmol) and MTC-allyl (210 mg, 1.050 mmol) were quickly added to the reaction and flask was re-sealed with septum. The reaction was allowed to stir at 70° C. for ~72 hours. To quench the reaction, methanol was added, and residual monomers were removed by crashing out the polymer in a vortexing solution of hexanes two times to yield slightly off-white polymer.

k. Poly(10% MTC-allyl, 90% MTC-Et) Nanoparticle Formation Using Thiol-Ene Cross-Linking With 3,6-dioxa-1,8-octanedithiol 3,6-dioxa-1,8-octane-dithiol (34.3 µL, 0.209 mmol) was added to a solution of poly(10% MTC-allyl, 90% MTC-Et) (100 mg, M$_n$=5.3 kDa, PDI=1.25) dissolved in CH$_2$Cl$_2$ (16.2 mL). The reaction mixture refluxed at 12 hours at 45° C. Residual dithiol was removed by dialyzing with SnakeSkin Pleated Dialysis Tubing (MWCO=10,000) against CH$_2$Cl$_2$ to yield particles (90 mg). $^1$H NMR (400 MHz, CDCl$_3$/TMS, ppm) δ: The significant change is the disappearance of the allylic protons at 5.9 and 5.3 ppm and the emergence of peaks at 3.64 ppm due to the methylene protons adjacent to the oxygens in the crosslinker and 2.73-2.68 ppm due to methylene protons adjacent to the sulfide functionality.

l. Poly(20% MTC-allyl, 80% MTC-Et) Nanoparticle Formation Using Thiol-Ene Cross-Linking With 3,6-dioxa-1,8-octanedithiol 3,6-dioxa-1,8-octane-dithiol (70.1 µL, 0.428 mmol) was added to a solution of poly(20% MTC-allyl, 80% MTC-Et) (100 mg, M$_n$=6.4 kDa, PDI=1.39) in CH$_2$Cl$_2$ (33.0 mL). The reaction mixture refluxed at 12 hours at 45° C. Residual dithiol was removed by dialyzing with SnakeSkin Pleated Dialysis Tubing (MWCO=10,000) against CH$_2$Cl$_2$ to yield particles (90 mg). $^1$H NMR (400 MHz, CDCl$_3$/TMS, ppm) δ: The significant change is the disappearance of the allylic protons at 5.8 and 5.3 ppm and the emergence of peaks at 3.64 ppm due to the methylene protons adjacent to the oxygens in the crosslinker and 2.73-2.68 ppm due to methylene protons adjacent to the sulfide functionality.

m. Poly(5% MTC-Epox, 95% MTC-Et) Nanoparticle Formation Using Epdxide-Amine Cross-Linking With 2,2'-ethylenedioxy-bis(ethylamine)

2,2'-ethylenedioxy-bis(ethylamine) (22.9 µL, 0.157 mmol) was added to a solution of poly(5% MTC-epox, 95% MTC-et) (140 mg, M$_n$=5.0 kDa, PDI=1.56) dissolved in CH$_2$Cl$_2$ (12.1 mL). The reaction mixture refluxed at 12 hours at 45° C. Residual bisamine was removed by dialyzing with Snakeskin Pleated Dialysis Tubing (MWCO=10,000) against CH$_2$Cl$_2$ to yield particles (130 mg). $^1$H NMR (400 MHz, CDCl$_3$/TMS, ppm) δ: The significant change is the disappearance of the epoxide ring protons at 3.19, 2.82, and 2.63 ppm and the emergence of peaks at 3.62-3.56 due to the methylene protons adjacent to the oxygens in the crosslinker and 3.36 ppm corresponding to the protons neighboring the secondary amine of the PEG linker after crosslinking.

n. Poly(10% MTC-Epox, 90% MTC-Et) Nanoparticle Formation Using Epdxide-Amine Cross-Linking With 2,2'-ethylenedioxy-bis(ethylamine)

2,2'-ethylenedioxy-bis(ethylamine) (27.0 µL, 0.187 mmol) was added to a solution of poly(10% MTC-epox, 90% MTC-et) (90 mg, $M_n$=5.3 kDa, PDI=1.25) dissolved in CH$_2$Cl$_2$ (14.4 mL). The reaction mixture refluxed at 12 hours at 45° C. Residual bisamine was removed by dialyzing with Snakeskin Pleated Dialysis Tubing (MWCO=10,000) against CH$_2$Cl$_2$ to yield particles (71 mg). $^1$H NMR (400 MHz, CDCl$_3$/TMS, ppm) δ: The significant change is the disappearance of the epoxide ring protons at 3.19, 2.82, and 2.63 ppm and the emergence of peaks at 3.62-3.56 due to the methylene protons adjacent to the oxygens in the cross-linker and 3.36 ppm corresponding to the protons neighboring the secondary amine of the PEG linker after cross-linking.

o. Poly(20% MTC-Epox, 80% MTC-Et) Nanoparticle Formation Using Epoxide-Amine Cross-Linking With 2,2'-ethylenedioxy-bis(ethylamine)

2,2'-ethylenedioxy-bis(ethylamine) (61.8 µL, 0.420 mmol) was added to a solution of poly(20% MTC-epox, 80% MTC-et) (100 mg, $M_n$=6.6 kDa, PDI=1.39) dissolved in CH$_2$Cl$_2$ (32.5 mL). The reaction mixture refluxed at 12 hours at 45° C. Residual bisamine was removed by dialyzing with Snakeskin Pleated Dialysis Tubing (MWCO=10,000) against CH$_2$Cl$_2$ to yield particles (74 mg). $^1$H NMR (400 MHz, CDCl$_3$/TMS, ppm) δ: The significant change is the disappearance of the epoxide ring protons at 3.19, 2.82, and 2.63 ppm and the emergence of peaks at 3.62-3.56 due to the methylene protons adjacent to the oxygens in the cross-linker and 3.36 ppm corresponding to the protons neighboring the secondary amine of the PEG linker after cross-linking.

p. Gel Permeation Chromatography(GPC) Traces of Poly(MAC-co-MTC-Et

Figure 9:
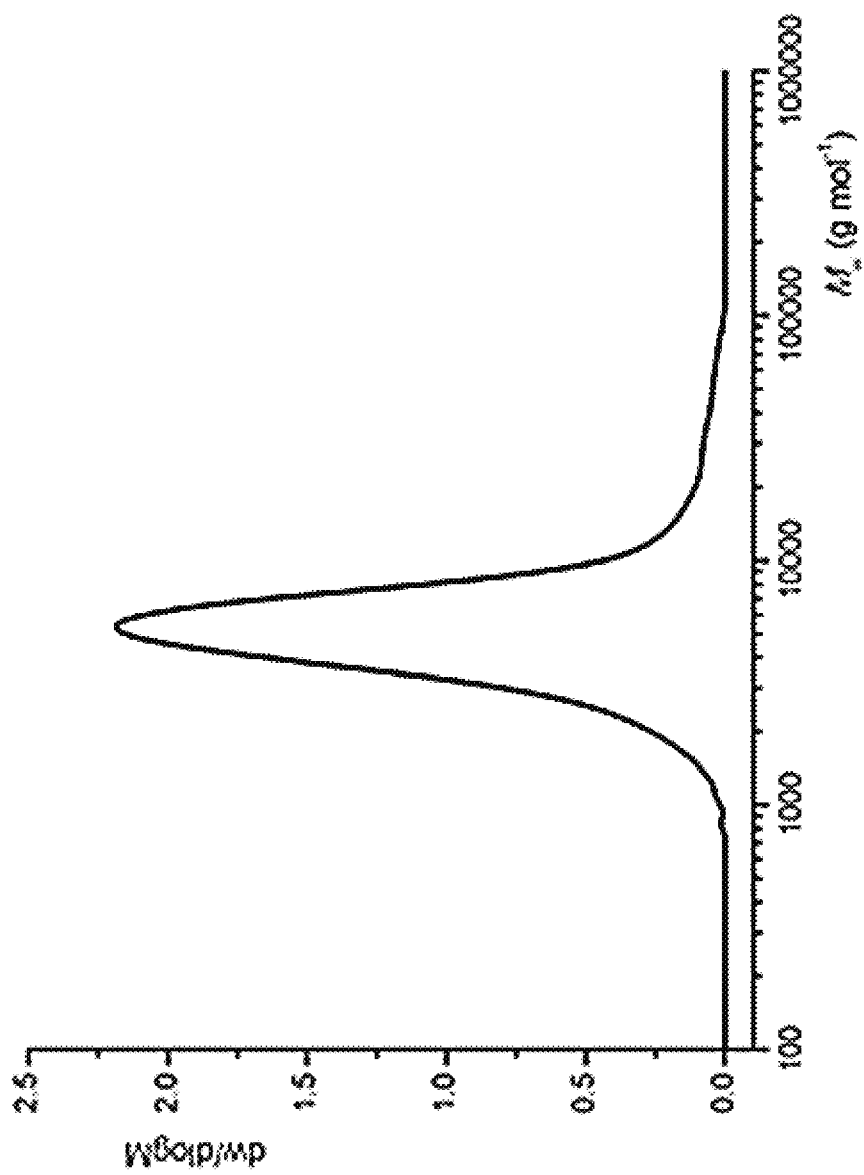
FIG. 9 shows the GPC trace of poly(MAC-co-MTC-Et) with comonomer ratio 5:95 (MAC:MTC-Et).

FIG. 9 shows the GPC trace of poly(MAC-co-MTC-Et) with comonomer ratio 5:95 (MAC:MTC-Et). The poly(MAC-co-MTC-Et) had a $M_{n(GPC)}$ of 4.7 kDa and a PDI of 1.56.

Figure 10:
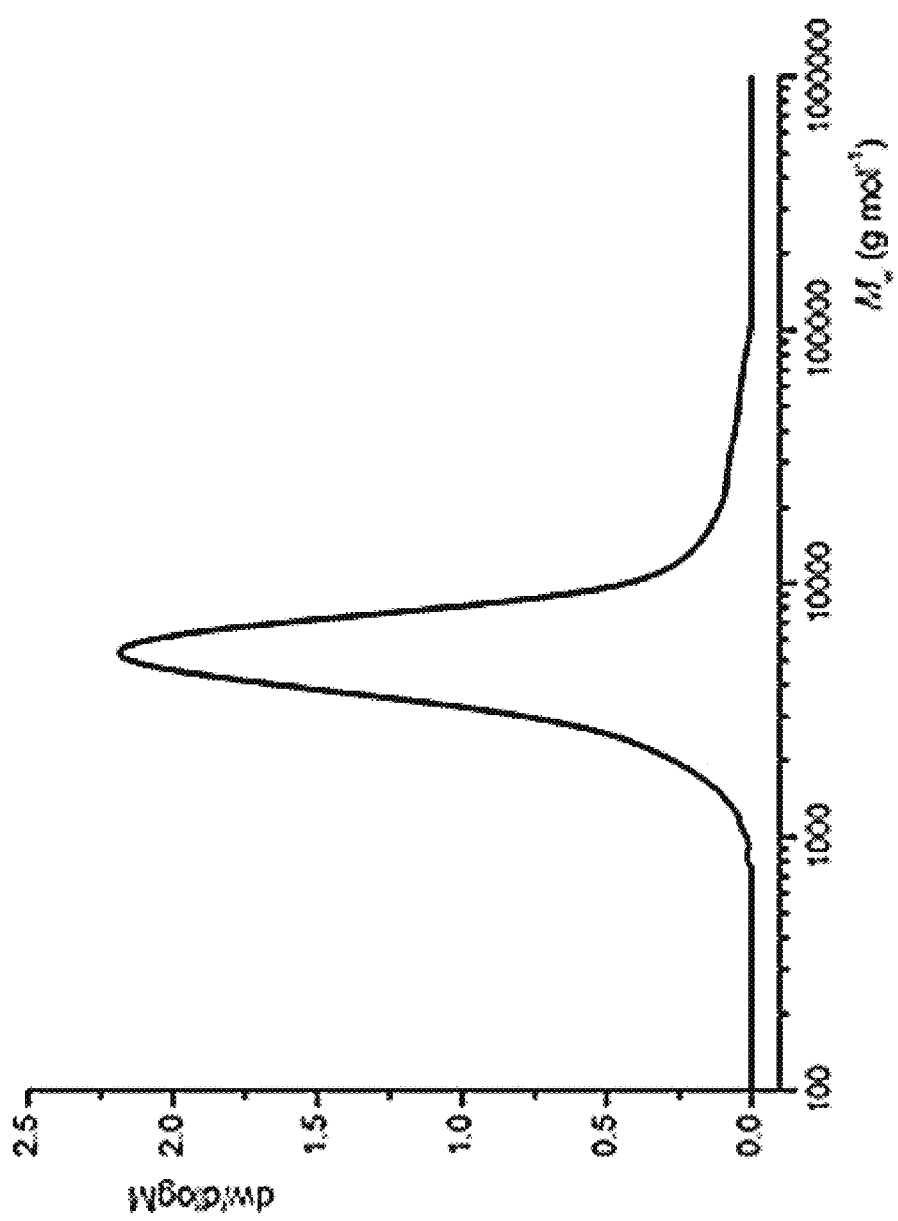
FIG. 10 shows the GPC trace of poly(MAC-co-MTC-Et) with comonomer ratio 10:90 (MAC:MTC-Et).

FIG. 10 shows the GPC trace of poly(MAC-co-MTC-Et) with comonomer ratio 10:90 (MAC:MTC-Et). The poly(MAC-co-MTC-Et) has a $M_{n(GPC)}$ of 5.0 kDa and a PDI of 1.25.

Figure 11:
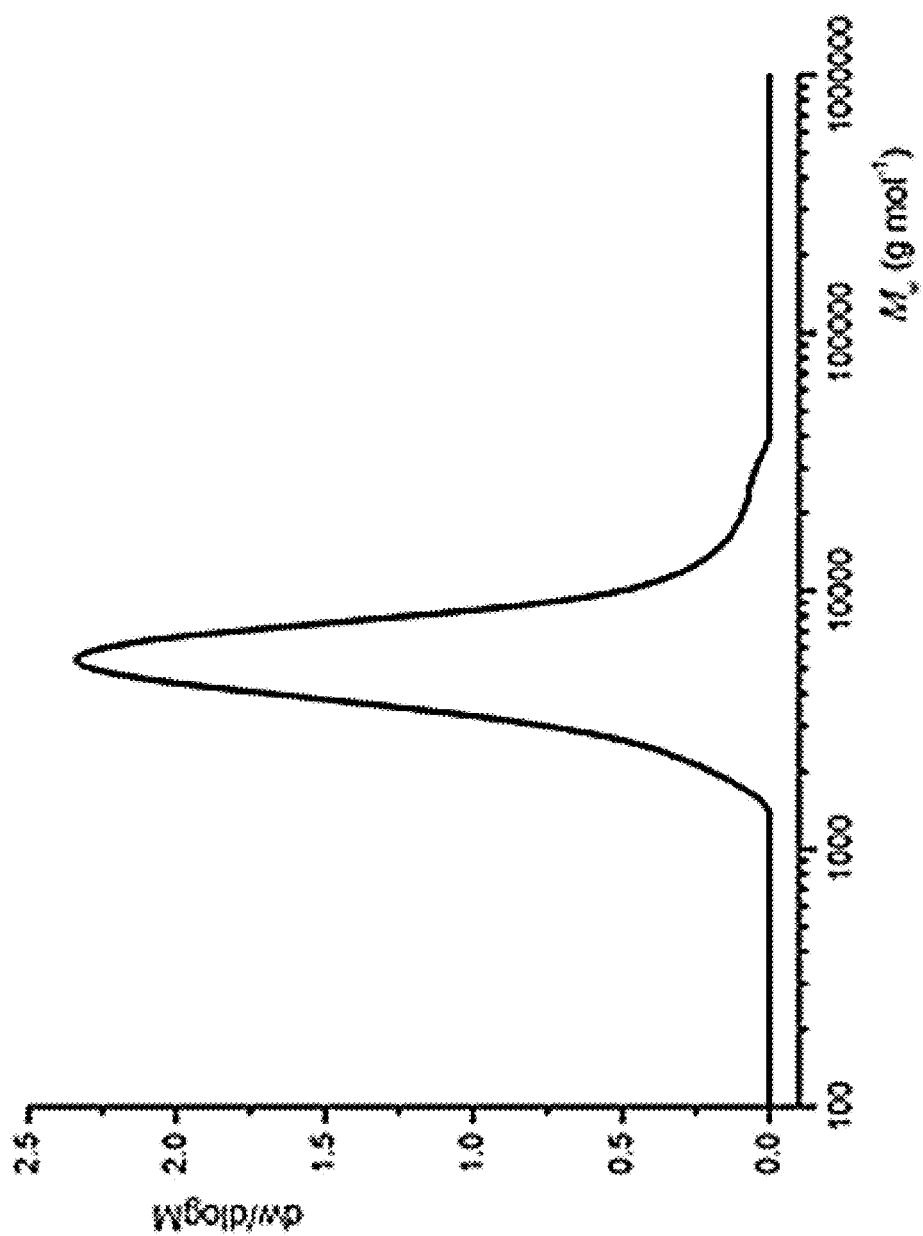
FIG. 11 shows the GPC trace of poly(MAC-co-MTC-Et) with comonomer ratio 20:80 (MAC:MTC-Et).

FIG. 11 shows the GPC trace of poly(MAC-co-MTC-Et) with comonomer ratio 20:80 (MAC:MTC-Et). The poly(MAC-co-MTC-Et) had a $M_{n(GPC)}$ of 4.9 KDa and a PDI of 1.39.

q. Oxidation of Carbonate Copolymers

General Reaction: Oxidation of poly(MTC-allyl, MTC-ethyl)

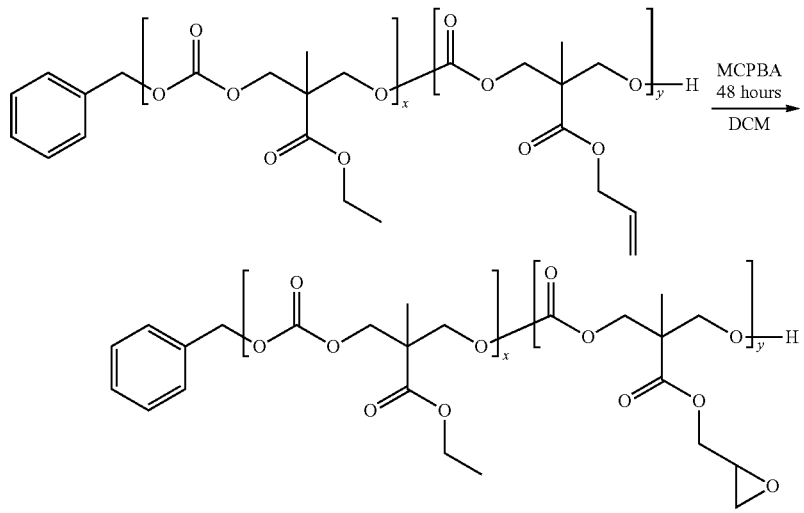

In a 25 mL round bottom flask equipped with a stir bar, polymer (0.369 g, 0.346 mmol) was dissolved in 6.8 mL dichloromethane and 3-chloroperoxybenzoic acid (83.6 mg, 0.485 mmol) was added. The mixture stirred for 48 hours at room temperature. Residual 3-chloroperoxybenzoic acid was removed by extracting the polymer solution in dichloromethane against aqueous sodium bicarbonate to yield polymer (NMR Mn=4941 Da, 16.0% MTC-epox, 1.8% MTC-allyl, 82.2% MTC-Et).

To determine the chain length more accurately we have changed the initiator from benzyl alcohol to 3-methyl-1-butanol. With the use of this initiator we have accurately prepared the molecular weight of the polycarbonate.

Synthesis of poly(MTC-Et) with 3-methyl-1-butanol ([mon]:[cat]:[init]=1250:4:50)

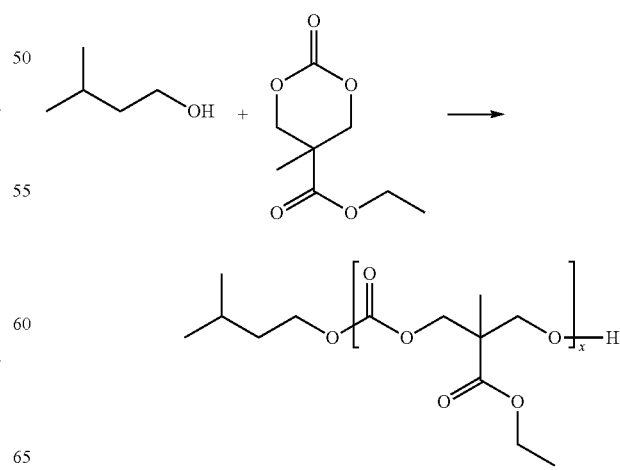

A 1-dram vial was equipped with a stir bar, capped with a rubber septum, argon purged and flame dried. Sn(OTf)$_2$ (3.5 mg, 0.008 mmol) was weighed directly into the vial. The vial was sealed with rubber septum, argon purged and set to stir in a 70° C. oil bath. 3-methyl-1-butanol (11.6 uL, 0.106 mmol) was added to the flask via microsyringe and the catalyst/initiator solution was allowed to stir at 70 C for 30 minutes. MTC-Et (0.500 g, 2.657 mmol) was added to the solution and allowed to stir. Reaction began slowing down at 26 hrs so I removed from heat. Crude NMR showed 71.8% monomer conversion and Mn=3,303 Da.

Synthesis of 10 k poly(MTC-Et) with 3-methyl-1-butanol ([mon]:[cat]:[init]=1250:4:25)

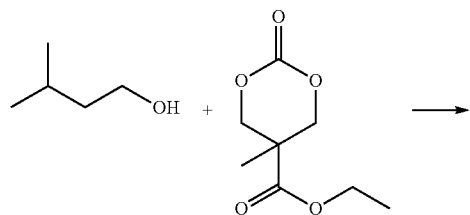

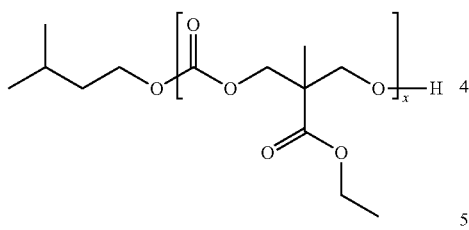

A 1-dram vial was equipped with a stir bar, capped with a rubber septum, argon purged and flame dried. Sn(OTf)$_2$ (3.5 mg, 0.008 mmol) was weighed directly into the vial. The vial was sealed with rubber septum, argon purged and set to stir in a 70° C. oil bath. 3-methyl-1-butanol (5.8 uL, 0.053 mmol) was added to the flask via microsyringe and the catalyst/initiator solution was allowed to stir at 70° C. for 30 minutes. MTC-Et (0.500 g, 2.657 mmol) was added to the solution and allowed to stir. Took out of oil bath after 70 hours and precipitated into ~150 mL of very cold methanol to yield colorless polymer (67 mg, Mn=10,076 Da).

Kinetics of poly(MTC-Et) with 3-methyl-1-butanol ([mon]:[cat]:[init]=1250:4:50)

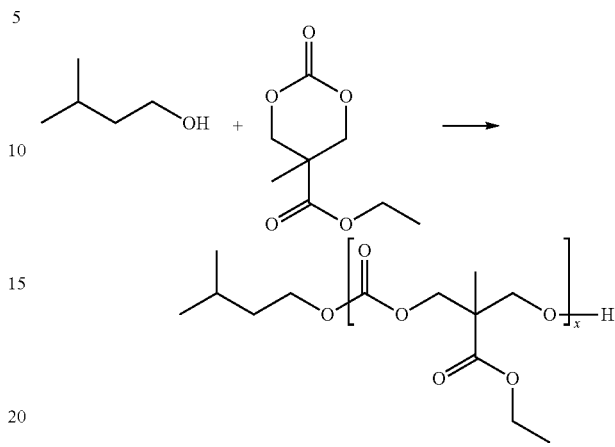

A 1-dram vial was equipped with a stir bar, capped with a rubber septum, argon purged and flame dried. Sn(OTf)$_2$ (3.5 mg, 0.008 mmol) was weighed directly into the vial. The vial was sealed with rubber septum, argon purged and set to stir in a 70° C. oil bath. 3-methyl-1-butanol (11.6 uL, 0.106 mmol) was added to the flask via microsyringe and the catalyst/initiator solution was allowed to stir at 70° C. for 30 minutes. MTC-Et (0.500 g, 2.657 mmol) was added to the solution and allowed to stir. At each time point, a small amount of the reaction was removed via syringe and analyzed by NMR.

Figure 12:
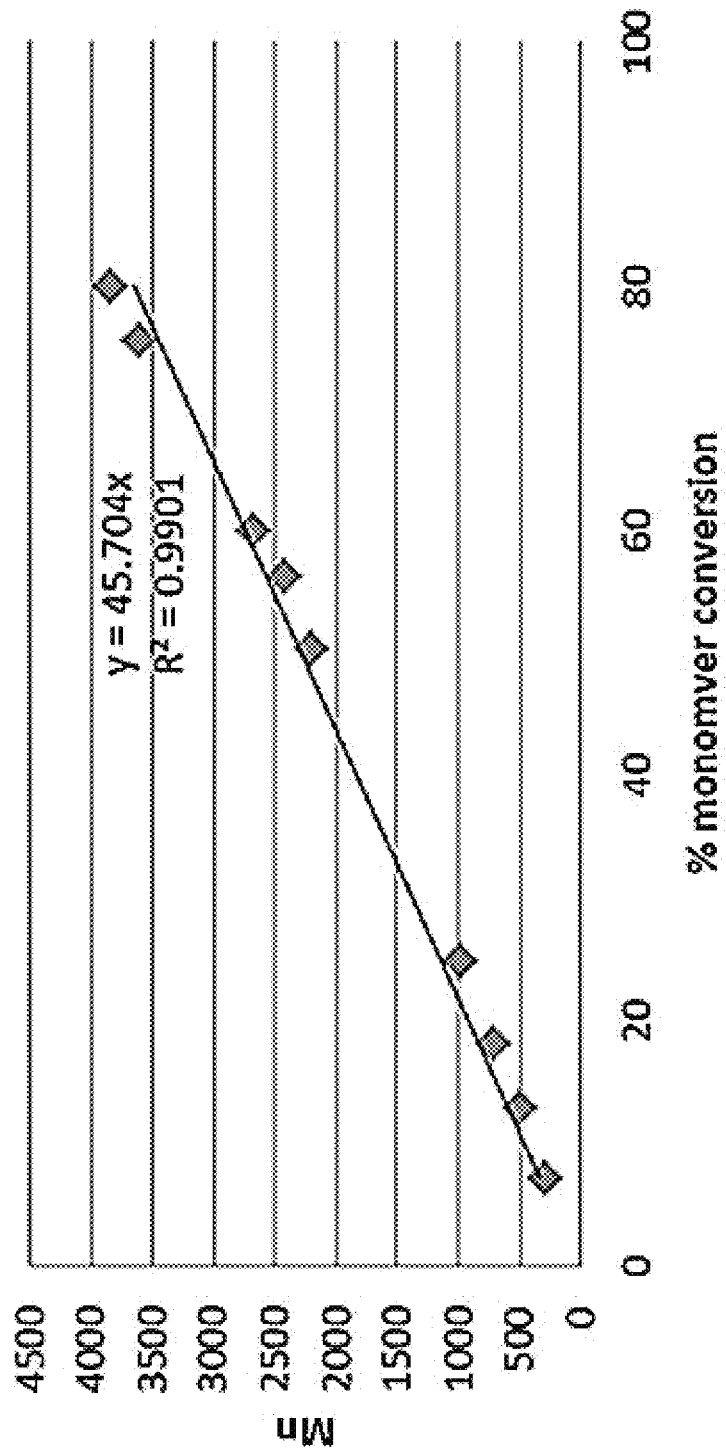
FIG. 12 shows the kinetic results for poly(MTC-Et) with 3-methyl-1-butanol with a [mon]:[cat]:[init] ration of 1250: 4:50.
Figure 13:
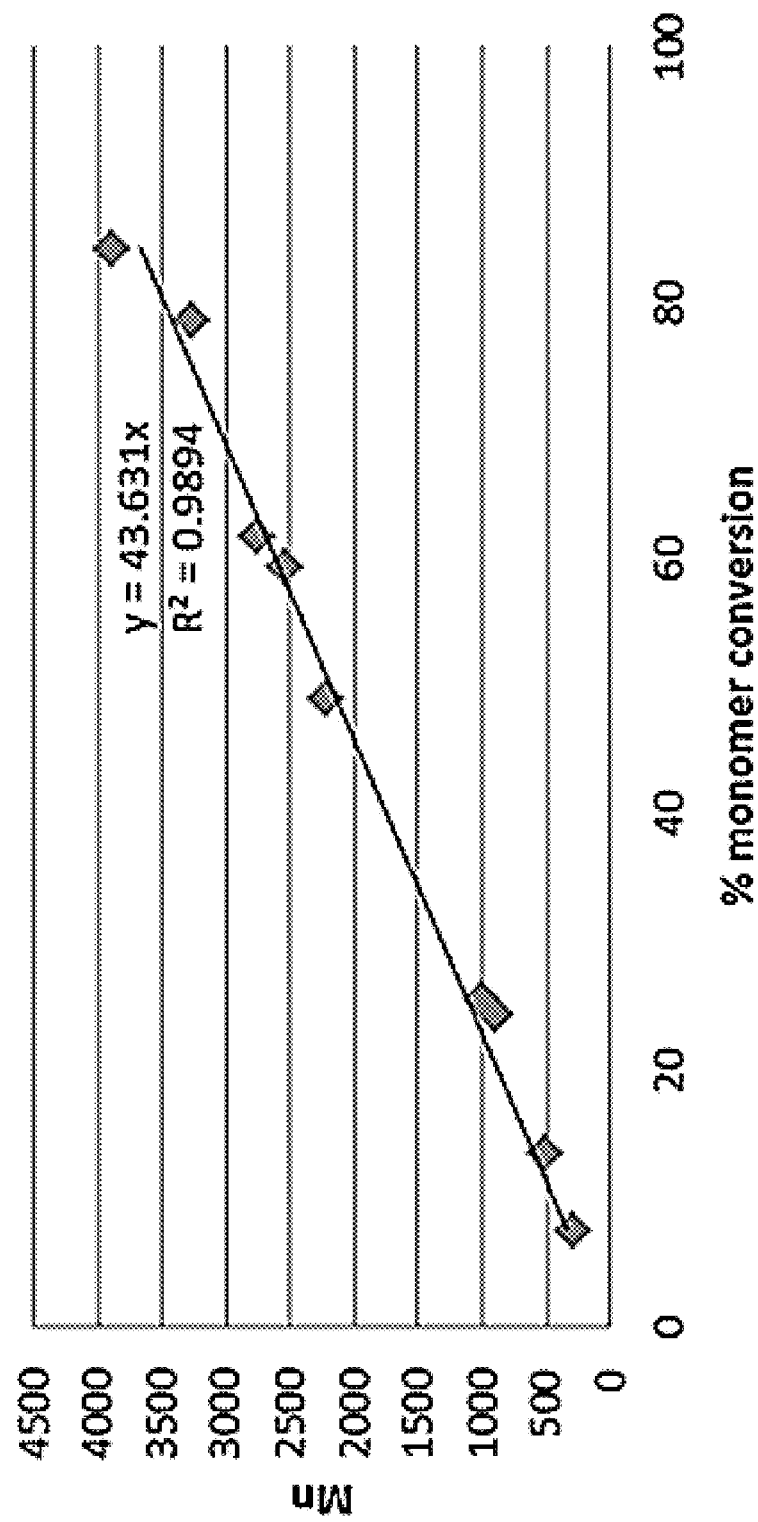
FIG. 13 shows the kinetic results for poly(MTC-Et) with 3-methyl-1-butanol with a [mon]:[cat]:[init] ration of 1250: 4:50.

The kinetic results for poly(MTC-Et) with 3-methyl-1-butanol with a [mon]:[cat]:[init] ration of 1250:4:50 can be seen in FIGS. 12 and 13.

r. Attachement of Pep T1 Targeting Peptide to Crosslinked Polymers (3S)-4-tert-butoxy-3-[[(2S)-2-(tert-butoxycarbonylamino)propanethioyl]amino]-4-oxo-butanoic acid (1.1 mg, 2.9 μmol) in anhydrous DMF (96 μL) stirred under argon at 0° C. with N-methylmorpholine (30 μL, 0.11 M in DMF, 3.3 μmol). Isobutyl chloroformate (30 μL, 0.11 M in DMF, 3.3 μmol) was added drop-wise and the reaction was allowed to stir 2 hours. A solution of nanoparticles (20 mg, 0.10 μmol) in anhydrous DMF (2.6 mL) was then added drop-wise and reaction was allowed to stir 24 hours at room temperature. The reaction was purified by dialysis with Snakeskin Pleated Dialysis Tubing (MWCO 10,000) against dichloromethane. $^1$H NMR (400 MHz, CDCl$_3$/TMS, ppm) δ: The significant change is the appearance of the tert-butoxy protons at 1.50 and 1.43 ppm due to the peptide attachment. The reaction is illustrated below.

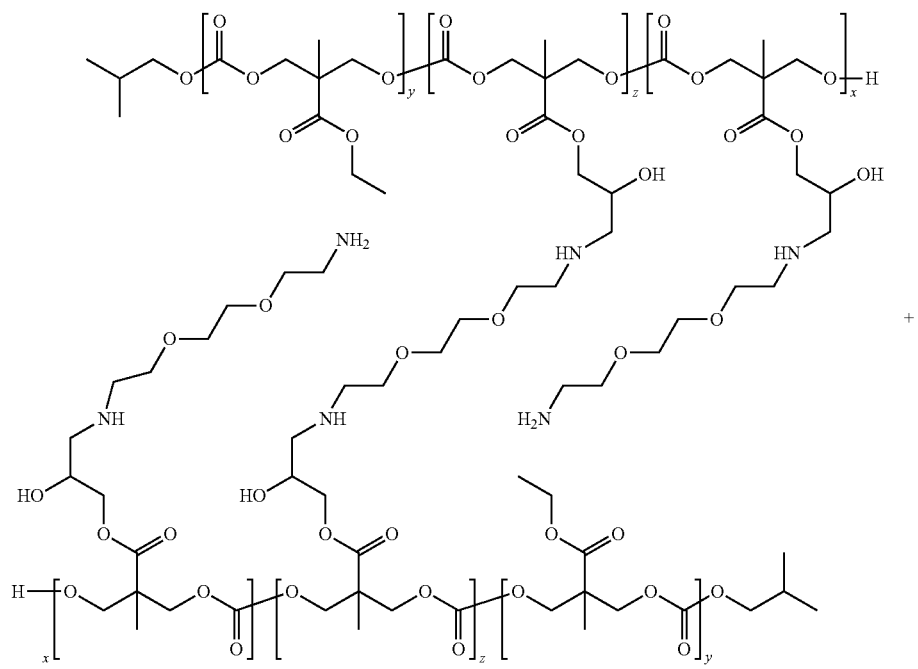
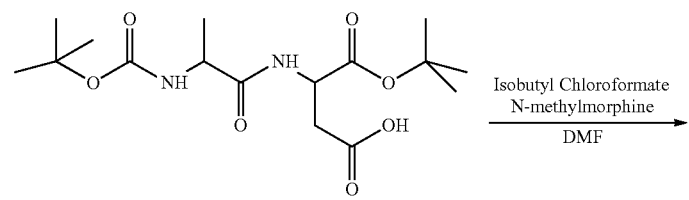
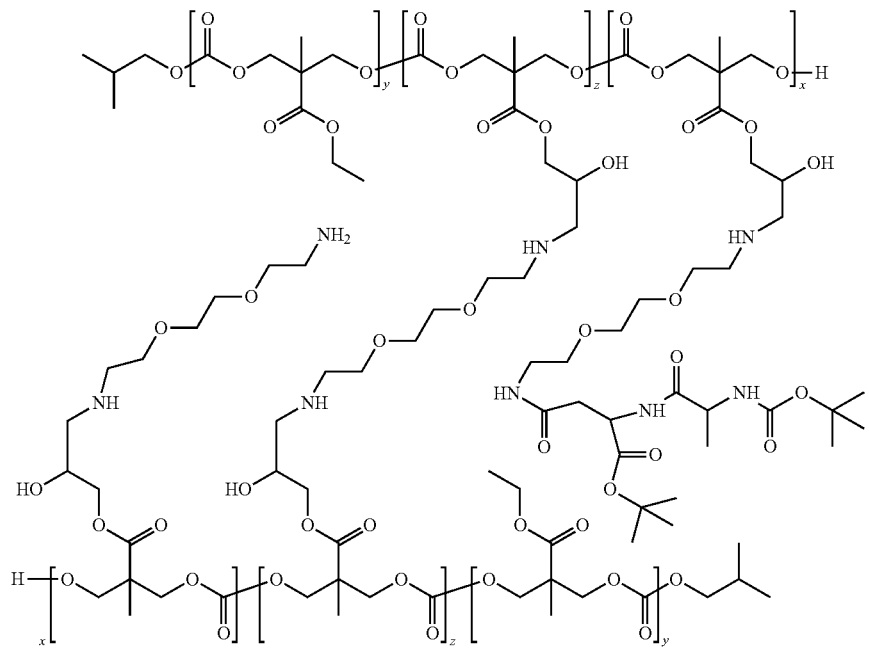

s. Encapsulation of Paclitaxel

A solution of nanoparticle (40 mg) and paclitaxel (8.8 mg) in DMSO (0.10 mL) was added drop-wise to a vortexing solution of aqueous 1% d-α tocopherol polyethyleneglycol (1000) succinate (Vit E-TPGS, 20 mL). The resulting precipitation was centrifuged at 7800 rpm for 20 minutes and supernatant was removed. The precipitation was freeze-dried to yield a clear, viscous liquid.

t. Polycarbonate Hydrogel Formation Via Thiolene Click

A mixture of poly(MEC, MAC) (100 mg, 0.10 mmol) and 2,2-dimethoxy-2-phenylacetophenone (DMPA, 5.4 mg, 0.02 mmol) was dissolved in DMF (0.10 mL) and allowed to stir at room temperature. 3,6-dioxa-1,8-octane-dithiol (17 uL, 0.10 mmol) was added and reaction was exposed to UV light (365 nm) for 5 minutes. The resulting gel was washed in sequence with methanol and dichloromethane and allowed to dry overnight in vacuo to yield a colorless gel. The reaction is illustrated below.

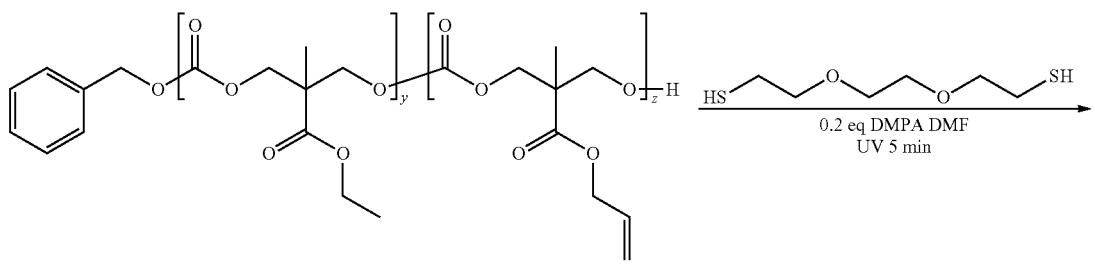

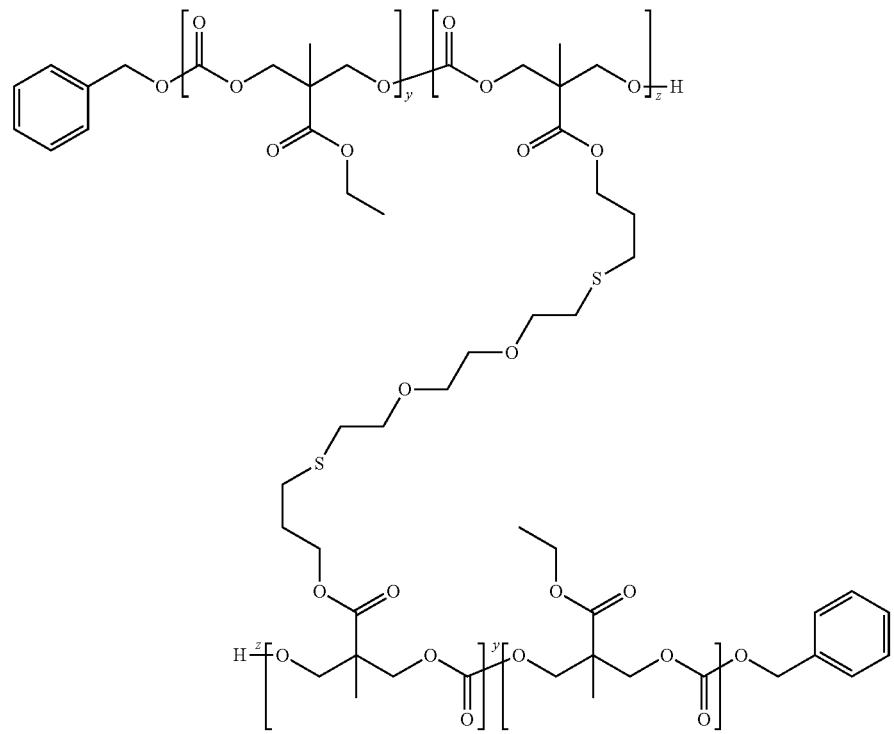

u. Polycarbonate/Hydroxyl Terminated Polymer Macroscopic Network Formation Via Thiolene Click
The poposed reaction is illustrated below.
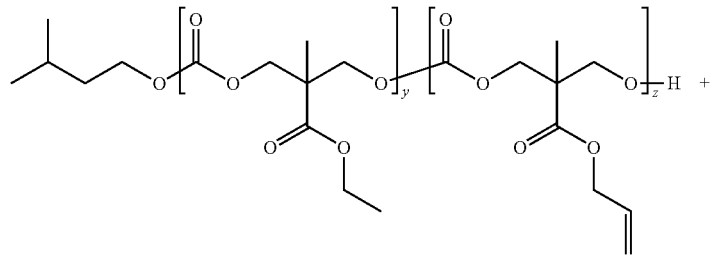
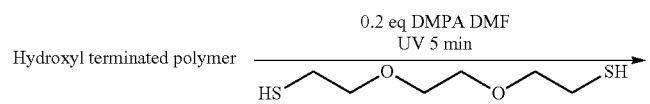
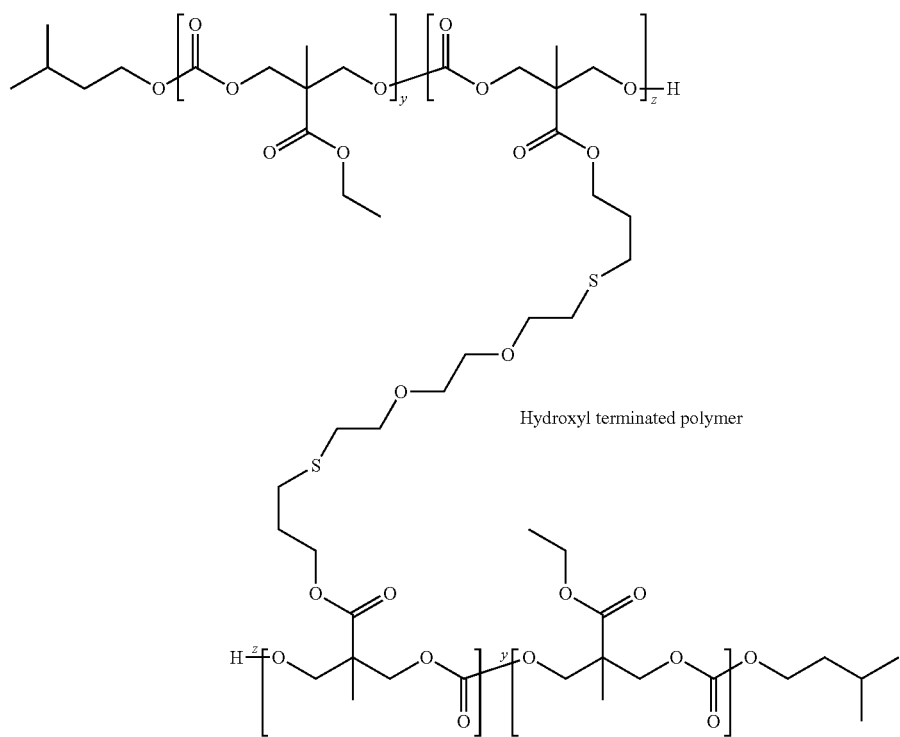

v. Polycarbonate/Hdroxyl Terminated Macroscopic Network
Formation Via Thiolene Click and Zinc Acetate Rearrangment
This poposed reaction is illustrated below.
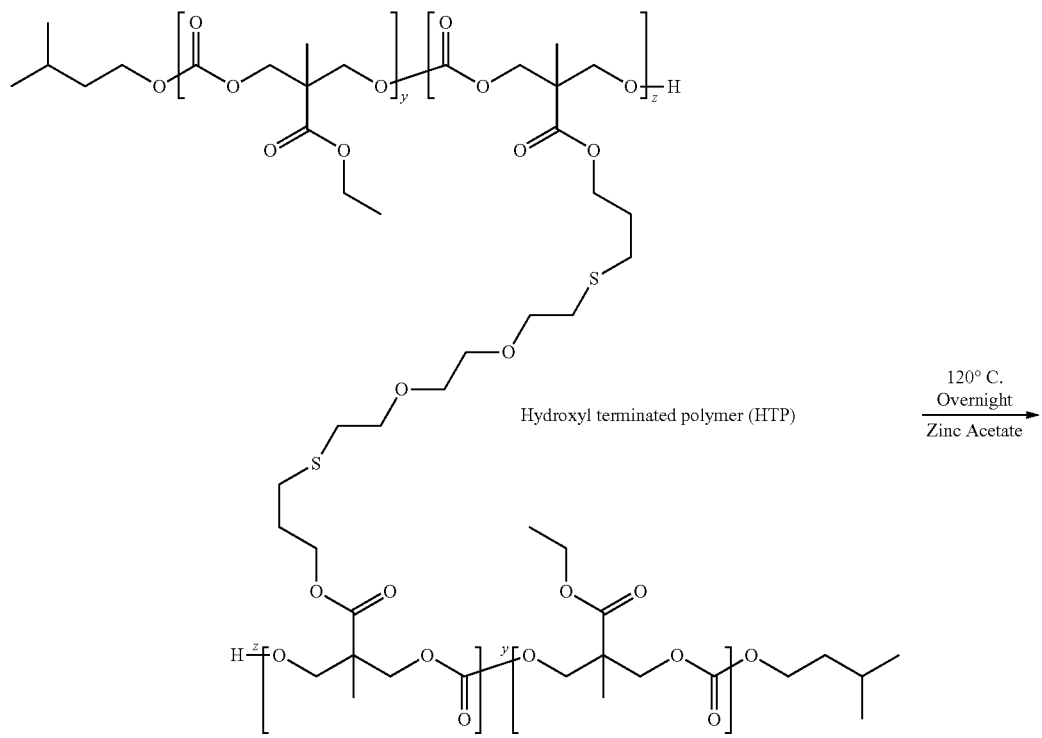
Hydroxyl terminated polymer (HTP)
120° C.
Overnight
Zinc Acetate
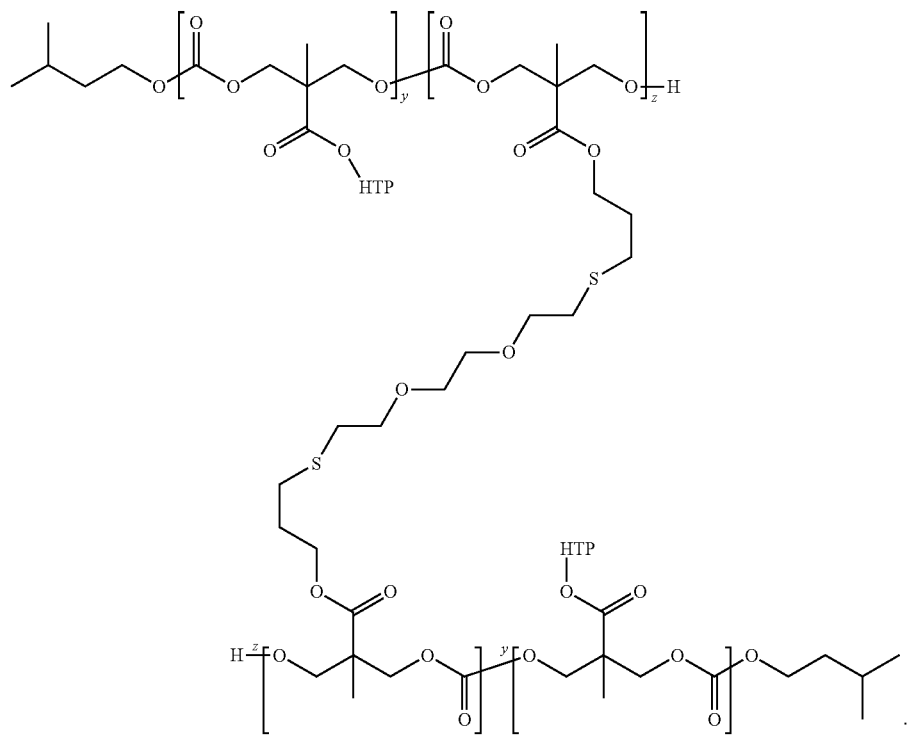

w. General MEC Homopolymer Synthesis

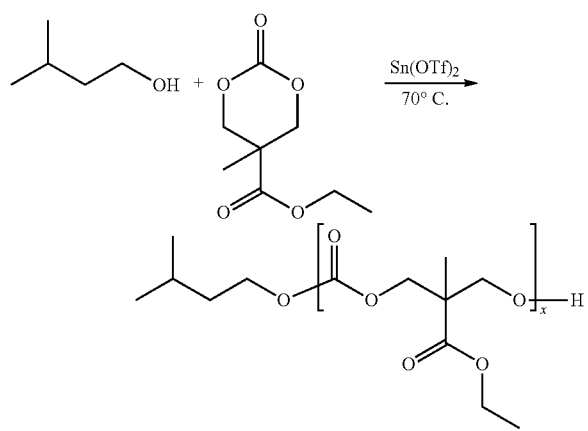

A 25-mL round bottom flask was equipped with stir bar, capped with rubber septum, flame dried and nitrogen purged. Sn(OTf)$_2$ (7.0 mg, 0.0168 mmol) was added to the flask, and the flask was nitrogen purged once more. 3-methyl-1-butanol (5.8 μL, 0.0531 mmol) was added to the reaction flask via microsyringe, and the catalyst/initiator mixture was allowed to stir at room temperature for 30 minutes. MEC (0.500 g, 2.657 mmol) was added to the flask and allowed to stir in 70° C. oil bath for 87 hours. Polymer was purified by precipitation into methanol or by using Spectra/Por dialysis membrane (MWCO=1,000 Da) against dichloromethane/methanol to yield colorless polymer (Theoretical Mn=18,800 Da, NMR Mn=18,400 Da, PDI=1.11 yield=0.460 g). $^1$H NMR (400 MHz, CDCl$_3$/TMS, ppm) δ: 4.40-4.15 (m, —OC(O)OCH$_2$), 1.30-1.22 (m, CH$_3$, —OCH$_2$CH$_3$), 0.93-0.91 (d, 3-methyl-1-butanol, —OCH$_2$CH$_2$CH(CH$_3$)$_2$).

x. General MEC, MAC Copolymer Synthesis

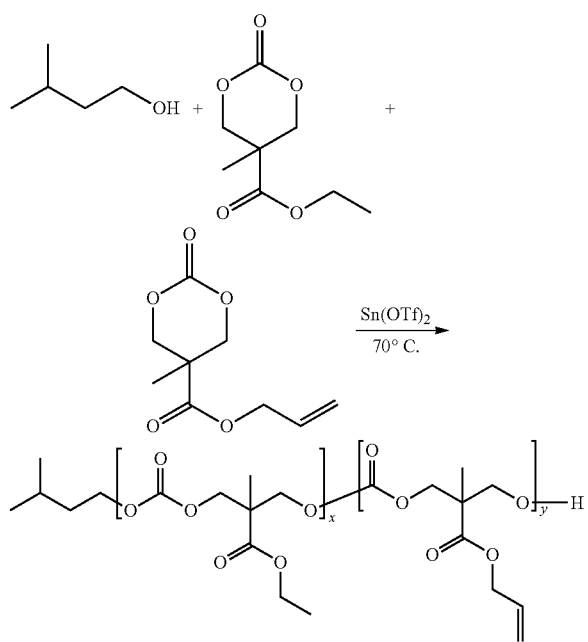

A 1-dram vial was equipped with stir bar, capped with rubber septum, flame dried and nitrogen purged. Sn(OTf)$_2$ (3.5 mg, 0.0084 mmol) was added to the vial, and the vial was nitrogen purged once more. 3-methyl-1-butanol (11.4 μL, 0.105 mmol) was added to the reaction vial by microsyringe, and the catalyst/initiator solution was allowed to stir at room temperature for 30 minutes. MEC (0.395 g, 2.099 mmol) and MAC (0.105 g, 0.5245 mmol) were added to the vial and allowed to stir in 70° C. oil bath for 71 hours. Polymer was purified by precipitation into methanol or by dialysis using Spectra/Por dialysis membrane (MWCO=1,000 Da) against methanol/dichloromethane to yield colorless polymer (Calculated Mn=4,800 Da, NMR Mn=6,500 Da, PDI=1.11, yield=0.359 g) theoretical allyl incorporation=20.0%, actual allyl incorporation=19.0%). $^1$HNMR (400 MHz, CDCl$_3$/TMS, ppm) δ: 5.91-5.85 (m, —OCH$_2$CHCH$_2$), 5.34-5.23 (m, —OCH$_2$CHCH$_2$), 4.64-4.62 (m, —OCH$_2$CHCH$_2$), 4.40-4.15 (m, MAC & MEC, —OC(O)OCH$_2$), 1.30-1.22 (m, MAC & MEC, CH$_3$; MEC, —OCH$_2$CH$_3$), 0.93-0.91 (d, 3-methyl-1-butanol, OCH$_2$CH$_2$CH(CH$_3$)$_2$). $^{13}$C NMR (400 MHz, CDCl$_3$/TMS, ppm) δ: 174.1, 172.1, 154.9, 154.4, 131.7, 118.5, 68.6, 65.9, 64.7, 61.2, 50.8, 48.2, 46.5, 24.8, 22.4, 17.5, 14.1.

y. Number Average Molecular Weight (MN)—Monomer Conversion Experiment

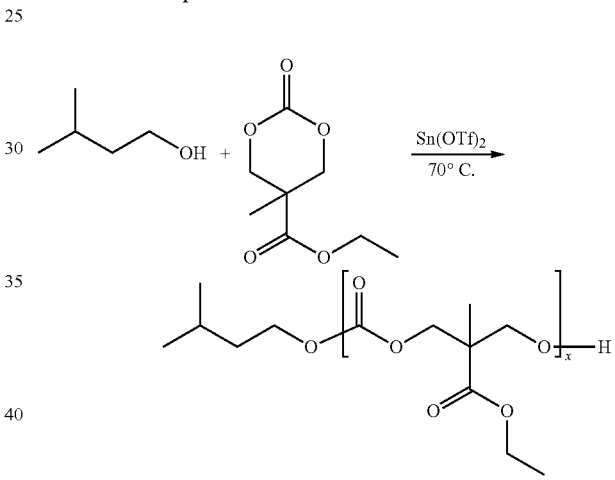

Figure 14:
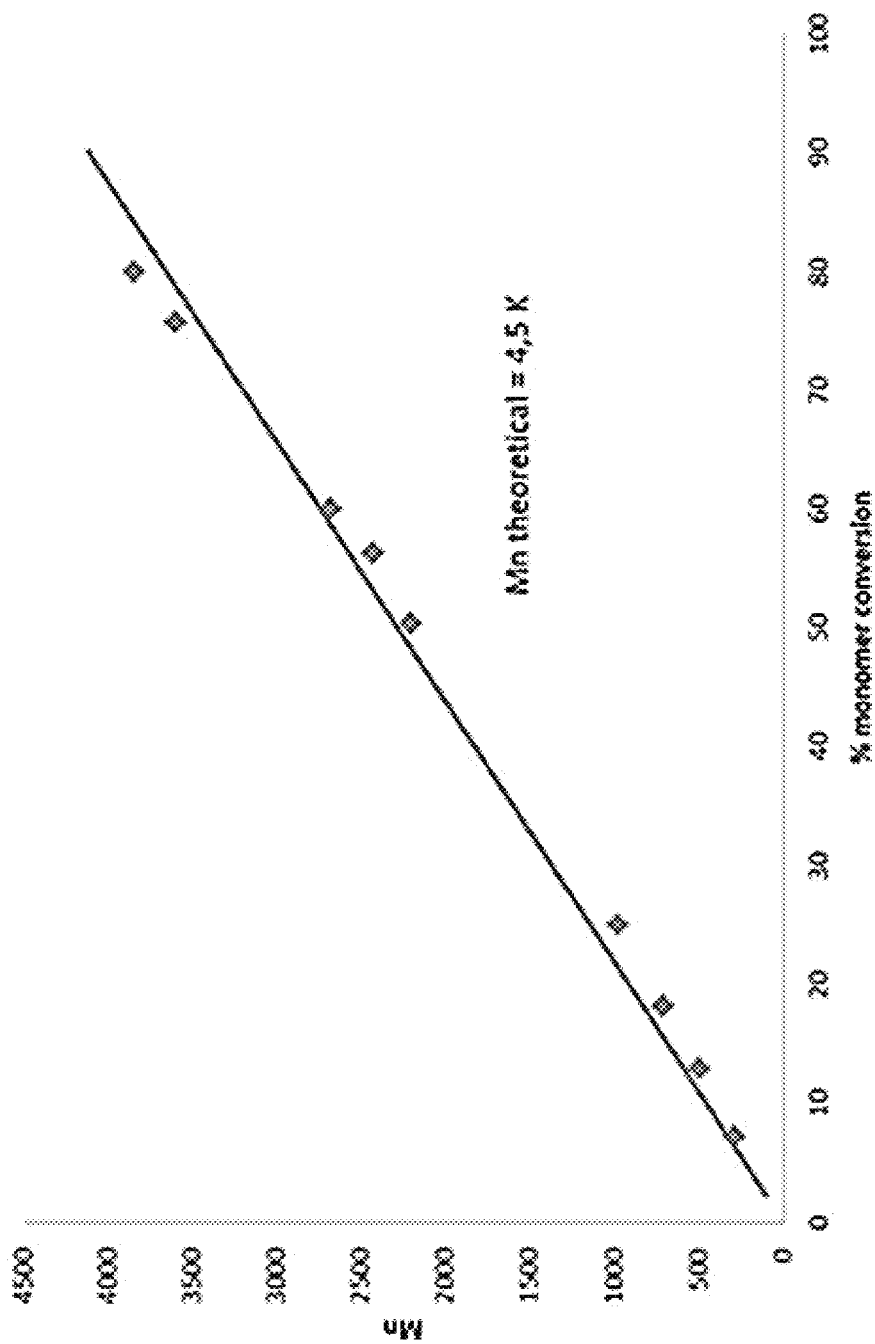
FIG. 14 shows the results for the monomer conversion experiment described herein.

The MEC homopolymers were prepared as described elsewhere herein. At predetermined time points, a small amount of the polymerization was removed and analyzed immediately by $^1$HNMR. The reaction yielded the results shown in FIG. 14.

REFERENCES (1) Beck, J. B.; Killops, K. L.; Kang, T.; Sivanandan, K.; Bayles, A.; Mackay, M. E.; Wooley, K. L.; Hawker, C. J. *Macromolecules* 2009, 42, 5629.
(2) Seo, M.; Beck, B. J.; Paulusse, J. M. J.; Hawker, C. J.; Kim, S. Y. *Macromolecules* 2008, 41, 6413.
(3) Ryu, J. H.; Chacko, R. T.; Jiwpanich, S.; Bickerton, S.; Babu, R. P.; Thayumanavan, S. *Journal of the American Chemical Society* 2010, 132, 17227.
(4) Ryu, J. H.; Jiwpanich, S.; Chacko, R.; Bickerton, S.; Thayumanavan, S. *Journal of the American Chemical Society* 2010, 132, 8246.
(5) van der Ende, A. E.; Kravitz, E. J.; Harth, E. *J. Am. Chem. Soc.* 2008, 130, 8706.
(6) van der Ende, A.; Croce, T.; Hamilton, S.; Sathiyakumar, V.; Harth, E. *Soft Matter* 2009, 5, 1417.

(7) van der Ende, A. E.; Harrell, J.; Sathiyakumar, V.; Meschievitz, M.; Katz, J.; Adcock, K.; Harth, E. *Macromolecules* 2010, 43, 5665.

(8) van der Ende, A. E.; Sathiyakumar, V.; Diaz, R.; Hallahan, D. E.; Harth, E. *Polymer Chemistry* 2010, 1, 93.

(9) Passarella, R. J.; Spratt, D. E.; van der Ende, A. E.; Phillips, J. G.; Wu, H. M.; Sathiyakumar, V.; Zhou, L.; Hallahan, D. E.; Harth, E.; Diaz, R. *Cancer Research* 2010, 70, 4550.

(10) Uhrich, K. E.; Cannizzaro, S. M.; Langer, R. S.; Shakesheff, K. M. *Chem Rev* 1999, 99, 3181.

(11) Albertsson, A. C.; Varma, I. K. *Adv Polym Sci* 2002, 157, 1.

(12) Drumright, R. E.; Gruber, P. R.; Henton, D. E. *Adv Mater* 2000, 12, 1841.

(13) Martina, M.; Hutmacher, D. W. *Polym Int* 2007, 56, 145.

(14) Rokicki, G. *Prog Polym Sci* 2000, 25, 259.

(15) Kamber, N. E.; Jeong, W.; Waymouth, R. M.; Pratt, R. C.; Lohmeijer, B. G. G.; Hedrick, J. L. *Chem Rev* 2007, 107, 5813.

(16) Bourissou, D.; Moebs-Sanchez, S.; Martin-Vaca, B. *Cr Chim* 2007, 10, 775.

(17) Dove, A. P.; Pratt, R. C.; Lohmeijer, B. G. G.; Culkin, D. A.; Hagberg, E. C.; Nyce, G. W.; Waymouth, R. M.; Hedrick, J. L. *Polymer* 2006, 47, 4018.

(18) Sanders, D. P.; Fukushima, K.; Coady, D. J.; Nelson, A.; Fujiwara, M.; Yasumoto, M.; Hedrick, J. L. *Journal of the American Chemical Society* 2010, 132, 14724.

(19) Wang, R.; Chen, W.; Meng, F. H.; Cheng, R.; Deng, C.; Feijen, J.; Zhong, Z. Y. *Macromolecules* 2011, 44, 6009.

(20) Xu, J. W.; Prifti, F.; Song, J. *Macromolecules* 2011, 44, 2660.

(21) Tempelaar, S.; Mespouille, L.; Dubois, P.; Dove, A. P. *Macromolecules* 2011, 44, 2084.

(22) Mullen, B. D.; Tang, C. N.; Storey, R. F. *J Polym Sci Pol Chem* 2003, 41, 1978.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of crosslinking polycarbonates comprising:
   (a) providing a first epoxy functionalized polycarbonate and a second epoxy functionalized polycarbonate; and
   (b) crosslinking the first epoxy functionalized polycarbonate and the second epoxy functionalized polycarbonate via a crosslinker,
   wherein the first epoxy functionalized polycarbonate comprises residues having the structures:

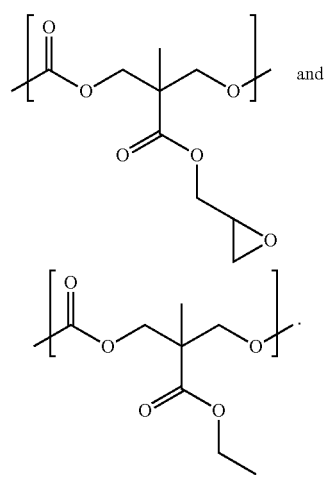

and

2. The method of claim 1, wherein the epoxy functionalizations are present as groups pendent from the polycarbonate backbone.

3. The method of claim 1, wherein crosslinking thereby forms a particle.

4. The method of claim 3, wherein the particle is a nanoparticle.

5. The method of claim 1, wherein the second epoxy functionalized polycarbonate comprises residues having the structure:

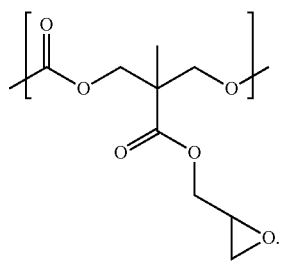

6. The method of claim 5, wherein the second epoxy functionalized polycarbonate further comprises residues having the structure:

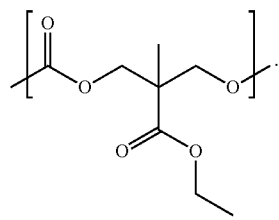

7. The method of claim 1, wherein the crosslinker comprises at least two moieties that can be reacted with the epoxy functionalities.

8. The method of claim 7, wherein the moieties are amine moieties.

9. The method of claim 1, wherein the crosslinker is

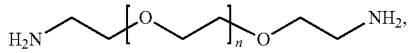

wherein n is from 1 to 1000.

10. The method of claim 1, wherein the crosslinker is

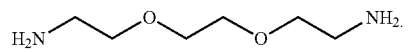

11. The method of claim 7, wherein the moieties are thiol moieties.

12. The method of claim 1, wherein the crosslinker is

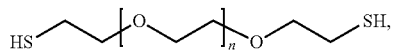

wherein n is from 1 to 1000.

13. The method of claim 1, wherein the crosslinker is

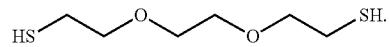

14. The method of claim 1, wherein the first epoxy functionalized polycarbonate and the second epoxy functionalized polycarbonate have the same structure.

15. The method of claim 1, wherein the first epoxy functionalized polycarbonate and the second epoxy functionalized polycarbonate are copolymers.

16. A method of crosslinking polycarbonates comprising:
(a) providing a first epoxy functionalized polycarbonate and the second epoxy functionalized polycarbonate; and
(b) crosslinking the first epoxy functionalized polycarbonate and the second epoxy functionalized polycarbonate via a crosslinker, wherein the first epoxy functionalized polycarbonate is

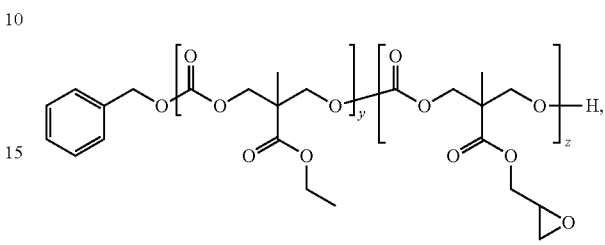

wherein y is 1 to 1000, and z is 1 to 1000.

17. The method of claim 16, wherein the first epoxy functionalized polycarbonate comprises at least 75% by weight of residues having a structure:

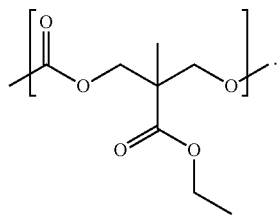

18. The method of claim 17, wherein the crosslinked polycarbonate has the structure:

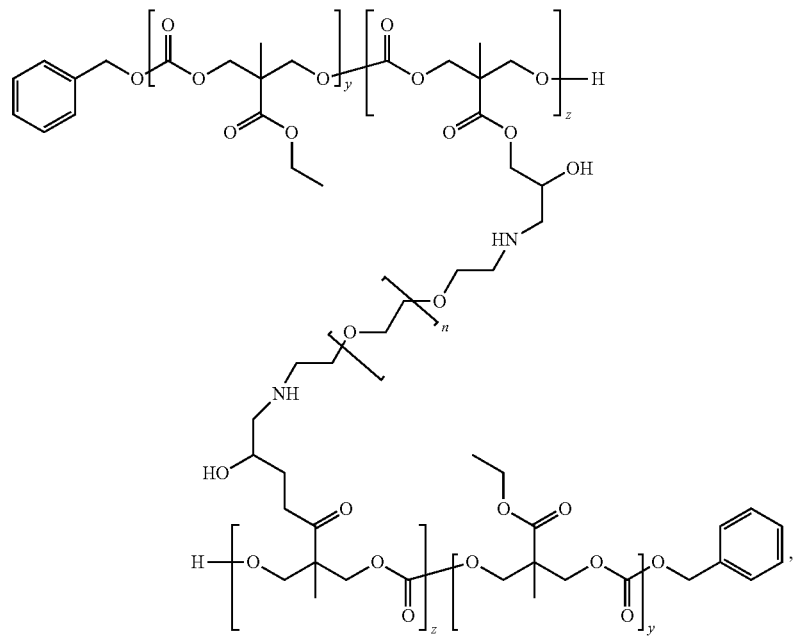

wherein each y is individually 1 to 1000, each z is individually 1 to 1000, and n is 1 to 1000.

19. A compound having a structure
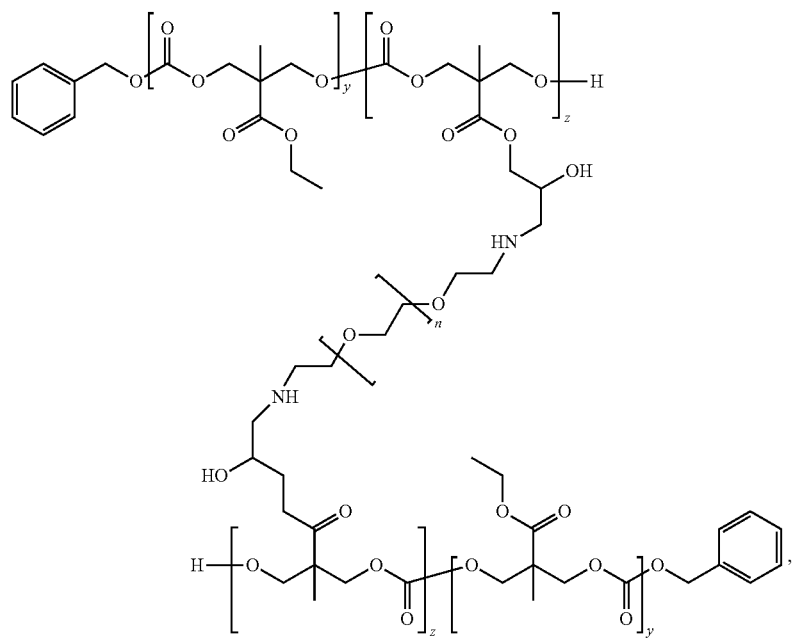
wherein each y is individually 1 to 1000, each z is individually 1 to 1000, and n is 1 to 1000.
20. A composition comprising the compound of claim 19.

UNITED STATES PATENT AND TRADEMARK OFFICE
CERTIFICATE OF CORRECTION

PATENT NO. : 10,308,774 B2
APPLICATION NO. : 15/443456
DATED : June 4, 2019
INVENTOR(S) : Eva M. Harth et al.

It is certified that error appears in the above-identified patent and that said Letters Patent is hereby corrected as shown below:

In the Specification

In Column 1, Lines 19-25, please replace:
"This invention was made with U.S. government support under grant number CHE-0645737, awarded by the National Science Foundation (NSF), and under grant number 5T32GM007628-33, awarded by the Pharmacology Training Grant under a National Institute of Health (NIH) Training Grant. The U.S. government has certain rights in the invention."

With:
-- This invention was made with government support under grant numbers EB009223 and GM007628 awarded by the National Institutes of Health and under grant number CHE0645737 awarded by the National Science Foundation. The government has certain rights in the invention. --

Signed and Sealed this
Nineteenth Day of November, 2019

Andrei Iancu
*Director of the United States Patent and Trademark Office*